(12) United States Patent  
Carlini et al.

(10) Patent No.: US 7,786,209 B2
(45) Date of Patent: Aug. 31, 2010

(54) NANOSTRUCTURED PARTICLES, PHASE CHANGE INKS INCLUDING SAME AND METHODS FOR MAKING SAME

(75) Inventors: Rina Carlini, Oakville (CA); Adela Goredema, Mississauga (CA); Marcel P. Breton, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 272 days.

(21) Appl. No.: 11/859,052

(22) Filed: Sep. 21, 2007

(65) Prior Publication Data
US 2008/0103250 A1    May 1, 2008

Related U.S. Application Data

(60) Provisional application No. 60/863,140, filed on Oct. 27, 2006.

(51) Int. Cl.
*C08L 83/00* (2006.01)
(52) U.S. Cl. .................. 524/588; 523/160; 523/161
(58) Field of Classification Search .................. 524/588
See application file for complete search history.

(56) References Cited

U.S. PATENT DOCUMENTS

| | | | |
|---|---|---|---|
| 3,172,892 A | 3/1965 | Le Suer et al. |
| 3,202,678 A | 8/1965 | Stuart et al. |
| 3,219,666 A | 11/1965 | Norman et al |
| 3,280,034 A | 10/1966 | Anzenberger et al. |
| 3,361,673 A | 1/1968 | Stuart et al. |
| 3,381,022 A | 4/1968 | Le Suer et al. |
| 3,442,808 A | 5/1969 | Traise et al. |
| 3,912,764 A | 10/1975 | Palmer, Jr. |
| 4,234,435 A | 11/1980 | Meinhardt et al. |
| 4,830,671 A | 5/1989 | Frihart et al. |
| 4,889,560 A | 12/1989 | Jaeger et al. |
| 4,889,761 A | 12/1989 | Titterington et al. |
| 5,145,518 A | 9/1992 | Winnik et al. |
| 5,146,087 A | 9/1992 | Van Dusen |
| 5,194,638 A | 3/1993 | Frihart et al. |

(Continued)

FOREIGN PATENT DOCUMENTS

EP    0 776 963 A1    6/1997

(Continued)

OTHER PUBLICATIONS

J.B. Carroll et al., "Self-assembly of gold nanoparticles through tandem hydrogen bonding and polyoligosilsequioxane (POSS)-POSS recognition processes," *Chem. Commun.*, pp. 1892-1893 (2002).

(Continued)

*Primary Examiner*—Vasu Jagannathan
*Assistant Examiner*—Doris L Lee
(74) *Attorney, Agent, or Firm*—Oliff & Berridge, PLC

(57) ABSTRACT

A hydrophobically- or hydrophilically-functionalized polyhedral oligomeric silsesquioxane has the following formula:

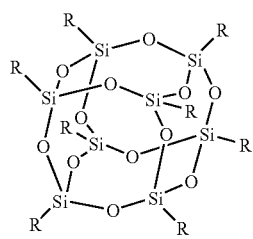

where each R, which can be the same or different, independently represents a linear, branched or cyclic organic group selected from the group consisting of hydrophobic alkyl groups, hydrophobic aryl groups, hydrophobic arylalkyl groups, hydrophobic cycloaliphatic groups, and hydrophilic organic moieties, provided that at least one of the R groups is a wax-like aliphatic group.

27 Claims, 2 Drawing Sheets

U.S. PATENT DOCUMENTS

| | | | |
|---|---|---|---|
| 5,202,265 A | 4/1993 | LaMora | |
| 5,208,630 A | 5/1993 | Goodbrand et al. | |
| 5,225,900 A | 7/1993 | Wright | |
| 5,231,135 A | 7/1993 | Machell | |
| 5,256,193 A | 10/1993 | Winnik et al. | |
| 5,271,764 A | 12/1993 | Winnik et al. | |
| 5,275,647 A | 1/1994 | Winnik | |
| 5,286,286 A | 2/1994 | Winnik et al. | |
| 5,286,799 A | 2/1994 | Harrison et al. | |
| 5,301,044 A | 4/1994 | Wright | |
| 5,319,030 A | 6/1994 | Harrison et al. | |
| 5,372,852 A | 12/1994 | Titterington et al. | |
| 5,378,574 A | 1/1995 | Winnik et al. | |
| 5,385,803 A | 1/1995 | Duff et al. | |
| 5,484,867 A | 1/1996 | Lichtenhan et al. | |
| 5,543,177 A | 8/1996 | Morrison et al. | |
| 5,554,480 A | 9/1996 | Patel et al. | |
| 5,597,856 A | 1/1997 | Yu et al. | |
| 5,621,022 A | 4/1997 | Jaeger et al. | |
| 5,645,632 A | 7/1997 | Pavlin | |
| 5,783,657 A | 7/1998 | Pavlin et al. | |
| 5,863,317 A | 1/1999 | Smith et al. | |
| 5,939,576 A | 8/1999 | Lichtenhan et al. | |
| 6,174,937 B1 | 1/2001 | Banning et al. | |
| 6,221,137 B1 | 4/2001 | King et al. | |
| 6,270,561 B1 | 8/2001 | Nguyen | |
| 6,472,076 B1 * | 10/2002 | Hacker | 428/447 |
| 6,472,523 B1 | 10/2002 | Banning et al. | |
| 6,664,024 B1 | 12/2003 | Nguyen et al. | |
| 6,713,614 B2 | 3/2004 | Carlini et al. | |
| 6,858,070 B1 | 2/2005 | Wong et al. | |
| 6,860,930 B2 | 3/2005 | Wu et al. | |
| 7,108,947 B2 | 9/2006 | Wu et al. | |
| 7,144,450 B2 | 12/2006 | Goredema et al. | |
| 7,220,300 B2 | 5/2007 | Goredema et al. | |
| 2003/0055193 A1 | 3/2003 | Lichtenhan et al. | |
| 2004/0163570 A1 * | 8/2004 | Vanmaele et al. | 106/31.13 |
| 2004/0261656 A1 | 12/2004 | Wu et al. | |
| 2006/0117992 A1 | 6/2006 | Goredema et al. | |
| 2006/0122415 A1 | 6/2006 | Carlini et al. | |
| 2006/0122416 A1 | 6/2006 | Goredema et al. | |
| 2006/0177748 A1 | 8/2006 | Wu et al. | |
| 2007/0119340 A1 | 5/2007 | Breton et al. | |

FOREIGN PATENT DOCUMENTS

| | | |
|---|---|---|
| EP | 1 452 569 A1 | 9/2004 |
| GB | 2 238 792 A | 12/1991 |
| JP | 2003-315959 A2 | 11/2003 |
| WO | WO 2004/041961 A1 | 5/2004 |
| WO | WO 2004/063207 | 7/2004 |
| WO | WO 2005/100444 | 10/2005 |

OTHER PUBLICATIONS

J.B. Carroll et al., "Electrostatic self-assembly of structured gold nanoparticles/polyhedral oligomeric silsesquioxane (POSS) nanocomposites," *Chem. Commun.*, pp. 690-694 (2004).

F.J. Feher et al., "A new route to incompletely-condensed silsesquioxanes: base-mediated cleavage of polyhedral oligosilsesquioxanes," *Chem. Commun.*, pp. 2309-2310 (1999).

F. Jeoung et al., "Surface modification via 'lock and key' specific self-assembly of polyhedral oligomeric silsesquioxane (POSS) derivatives to modified gold surfaces," *Chem. Commun.*, pp. 1510-1511 (2002).

J.D. Lichtenhan, "Silsesquioxane-based polymers," *Polymers Materials Encyclopedia*, J.C. Salamone, Ed., CRC Press: Boca Raton, FL, pp. 7768-7778 (1996).

C. McCusker et al., "cationic polyhedral oligomeric silsesquioxane (POSS) units as carriers for drug delivery processes," *Chem. Commun.*, pp. 996-998 (2005).

D.A. Schiraldi et al., "Polyester/POSS nanocomposite fibers," *Polymer Materials Science and Engineering*, 90, pp. 46-48 (2004).

L. Zheng, et al., "X-ray characterizations of polyethylene polyhedral oligomeric silsesquioxane copolymers," *Macromolecules*, 35, pp. 2375-2379 (2002).

L. Zheng, et al., "Polymer nanocomposites through controlled self-assembly of cubic silsesquioxane scaffolds," *Macromolecules*, 37, pp. 8606-8611 (2004).

* cited by examiner

NANOSTRUCTURED PARTICLES, PHASE CHANGE INKS INCLUDING SAME AND METHODS FOR MAKING SAME

CROSS REFERENCE TO RELATED APPLICATIONS

This application is a non-provisional application of U.S. Provisional Application No. 60/863,140 filed Oct. 27, 2006. The entire disclosure of the provisional application is incorporated herein by reference.

TECHNICAL FIELD

This disclosure is generally directed to nanostructured particles, and methods for making and using such nanostructured particles. More specifically, this disclosure is directed to nanostructured particles comprising self-assembled, hydrophobically- or hydrophilically-functionalized polyhedral oligomeric silsesquioxane. Such particles are useful, for example, as nanoscopic fillers for such compositions as inks and the like, such as phase change ink compositions.

RELATED APPLICATIONS

Commonly assigned, U.S. patent application Ser. No. 11/053,856 filed Feb. 10, 2005, describes an imaging member comprising: a substrate, a charge generating layer, and a charge transport layer, wherein an external layer of the imaging member comprises a polyhedral oligomeric silsesquioxane modified silicone dispersed therein. The polyhedral oligomeric silsesquioxane modified silicone can be formed by a reaction selected from the group consisting of: a hydrosilation reaction of a substituted polyhedral oligomeric silsesquioxane monomer with a hydridosilane or a hydride functional siloxane polymer; a peroxide activated cure reaction of a vinyl-substituted polyhedral oligomeric silsesquioxane monomer with at least one member selected from the group consisting of a polysiloxane, a vinyl-terminated polysiloxane, and a siloxane-vinyl-terminated siloxane copolymer; or a sol-gel reaction of at least one monomer selected from the group consisting of an alkoxysilane-substituted polyhedral oligomeric silsesquioxane, a silanol-substituted polyhedral oligomeric silsesquioxane, and a chlorosilane-substituted polyhedral oligomeric silsesquioxane with at least one member selected from the group consisting of an alkoxysilane, a chlorosilane, a silanol-terminated polysiloxane.

Commonly assigned, U.S. patent application Ser. No. 10/739,212 filed Dec. 19, 2003, describes a photoconductive imaging member comprising: a hole blocking layer; a photogenerating layer; a charge transport layer; and an optional overcoating layer; wherein at least one of the charge transport layer and the optional overcoating layer is formed in a sol-gel process. The sol-gel process can include, as a sol-gel precursor material, a modified polyhedral oligomeric silsesquioxane such as triethoxysilylisobutyl-polyhedral oligomeric silsesquioxane or octa(trichlorosilylethyl)polyhedral oligomeric silsesquioxane.

The appropriate components and process aspects of each of the foregoing may be selected for the present disclosure in embodiments thereof, and the entire disclosure of the above-mentioned applications are totally incorporated herein by reference.

REFERENCES

J. D. Lichtenhan, in *Polymeric Materials Encylcopedia*; J. C. Salamone, Ed. CRC Press: Boca Raton, Fla., 1996, pp. 7768-7778, discloses silsesquioxane materials, and particularly polyhedral oligomeric silsesquioxane (POSS) materials, and their preparation.

In L. Zheng, et al. *Macromolecules,* 2004, 37, 8606; and as discussed in references #9-11 and #13-33 cited therein, a polymeric nanocomposite material was prepared containing POSS spheres that were functionalized at one corner of the silsesquioxane cage with a long amorphous polymer chain (polybutadiene, PBD). They reported that the POSS-PBD copolymer materials had self-assembled to a lamella-like nanostructure resembling a bilayer, where the POSS spheres were packed hexagonally within a plane and two planes were stacked together (see FIG. 1). Furthermore, the covalently attached polymer chains acted as a physical barrier to close-packing of the POSS spheres, thereby resulting in the formation of two-dimensional raft-like nanostructures. As used herein, the prefix "nano" and the term "nanoscale" refer to particles or structures having at least one dimension measured in units of from 1 to about 100 nanometers, and "microscale" refers to particles or structures having at least one dimension measured in units of from 0.5 to about 100 micrometers.

In a second report by Zheng et al., L. Zheng, et al. *Macromolecules,* 2002, 35, 2375, is described the synthesis and characterization of novel polymer nanocomposites prepared by copolymerization of polyethylene with POSS-containing macromonomers. The polyethylene-POSS nanocomposite copolymer were found to aggregate and crystallize as nanocrystals, and were proposed to provide improved dimensional stability and thermal oxidative resistance.

U.S. Pat. Nos. 5,484,867 and 5,939,576 disclose processes for forming POSS compounds. For example, U.S. Pat. No. 5,484,867 discloses a process for the preparation of reactive POSS monomers that can be chemically reacted with oligomers, polymers, catalysts or co-monomers to form polyhedral silsesquioxane polymers containing silsesquioxanes as pendant, block, or end group segments. As another example, U.S. Pat. No. 5,939,576 discloses a process for the preparation of reactive POSS by metal catalyzed hydrosilylation reactions of silane containing POSS with olefinic reagents bearing functionalities useful for grafting reactions, polymerization chemistry and sol-gel process.

U.S. Patent Application Publication No. 2007/0119340 A1 describes an ink carrier comprising (A) a colloidal dispersion of at least one of nanoparticles and metal oxide nanoparticles exhibiting a substantially uniform distribution of said nanoparticles discretely distributed therewithin, said ink carrier being resistant to substantial aggregation of said nanoparticles distributed therewithin.

The disclosures of each of the foregoing references are hereby incorporated by reference herein in their entireties. The appropriate components and process aspects of the each of the foregoing references may also be selected for the present compositions and processes in embodiments thereof.

BACKGROUND

A printing ink is generally formulated according to strict performance requirements demanded by its intended market application and desired properties. Whether formulated for office printing or for production printing, a particular ink is expected to produce images that are robust and durable under stress conditions, such as exposure to abrasive or sharp objects or actions that produce a crease defect in the image (such as folding or scratching the imaged paper). For example, in a typical design of a piezoelectric ink jet device, the image is applied by jetting appropriately colored inks during four to six rotations (incremental movements) of a substrate (an image receiving member or intermediate transfer member) with respect to the ink jetting head, i.e., there is a small translation of the printhead with respect to the substrate in between each rotation. This approach simplifies the printhead design, and the small movements ensure good droplet registration. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops.

Hot melt inks that are typically used with ink jet piezoelectric printers have a wax based ink vehicle, e.g., a crystalline wax. Such solid ink jet inks provide vivid color images. In such systems, these crystalline wax inks partially cool on an intermediate transfer member and are then pressed into the image receiving medium such as paper. Transfuse spreads the image droplet, providing a richer color and lower pile height. The low flow of the solid ink also prevents show through on the paper. However, the use of crystalline waxes places some limitations on ink performance, for example the brittleness of crystalline materials may reduce the ink's robustness properties that are required to provide abrasion-resistant images. Consequently, inks that are formulated to have increased mechanical robustness properties are attractive materials.

There are several approaches on how to improve the robustness of solid inks. However, the right solution could be one that utilizes a new specialized material component that has not been explored for inks, but that have shown promise when used in other composite materials and applications. An example of such an enabling material is the POSS macromolecule, which are known to form self-assembled nanostructures. POSS is known as Polyhedral Oligomeric Silsesquioxanes, a family of molecularly precise organosilicon compounds that have a cubic structure comprised of a $Si_8O_{12}$ cage-like core and surrounded by eight functional organic groups that can be variable in structure, represented by the groups (which can be the same or different) in the following structure:

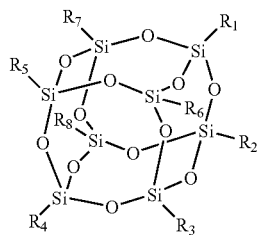

The POSS molecule itself has an approximate diameter of 1-3 nm in cases when the eight R groups are organic groups of less than about 6 carbons in length (for example, when the groups are cycloaliphatic groups such as cyclopentyl, or linear alkyl groups with less than 6 carbons such as iso-propyl), whereby the cubic silsesquioxane unit can be regarded as nearly "spherical" in shape.

POSS compounds have been reportedly used to synthesize polymer nanocomposite materials that function to reinforce polymeric binder materials such as epoxy resins, and are known to provide enhanced strengthening properties to materials (See J. D. Lichtenhan, cited above), in a similar manner as polymer-clay nanocomposites. However the disadvantages with using nanoclay materials as reinforcing fillers are the challenges with energy-intensive top-down processing that is needed to disperse the individual, exfoliated clay layers or platelets within the polymer binder. Alternatively, by using a nanoscale material component such as POSS that can be dispersed at the molecular level, one can take advantage of a self-assembly process to build a nanostructured layer that may function as the reinforcing filler component for a binder material, with the potential to produce nanocomposite materials having enhanced mechanical properties. Many substituted POSS compounds having a wide variety of organic R-groups and functional groups are commercially available from Hybrid Plastics Inc., and some have been investigated for various uses.

There remains a need for specialized components and/or composite materials that can be formulated in wax-based solid inks or other inks as reinforcing fillers that will enable improved mechanical robustness of the ink.

SUMMARY

The present disclosure addresses these and other needs, by providing nanostructured particles, such as nanostructured particles comprising self-assembled, functionalized polyhedral oligomeric silsesquioxane, which can be used as nanoscopic reinforcing fillers for such compositions as phase-change inks and the like.

An ordered nanocomposite material prepared from hydrophobically-modified POSS particles can improve robustness properties for wax-based solid inks. The improvement is believed to be beyond that provided by conventional filler materials. In embodiments, the POSS molecules are specifically designed to self-assemble into a scaffold-like lamellar nanostructures, which structure can be used, for example, to reinforce the wax vehicle of solid ink. The self-assembly of the POSS particle can be controlled so that the resulting nanostructure will have desired dimensions, such as below 100 nm, thereby maintaining desirable rheological and dispersion properties for jettability of the ink through a piezoelectric printhead device.

This disclosure provides hydrophobically-functionalized Polyhedral Oligomeric Silsesquioxane (POSS) materials that can self-assemble into lamellar nanostructures with dimensions, for example, in the region of 1-100 nm. The nanostructured hydrophobically-functionalized POSS compounds are suitable for use as nanoscale reinforcing filler materials (nano-fillers) that can offer significantly improved abrasion resistance, and hence image robustness, for solid wax-based inks. POSS is a precise organosilicate compound with a highly ordered cubic cage structure, and when at least one R-group is functionalized with a long aliphatic/hydrophobic carbon chain, can behave much like a surfactant where the aliphatic alkyl chain groups align together as hydrophobic "tail" groups and the cubic organosilicate groups align together like polar "head" groups. Such structural features of the hydrophobically-functionalized POSS can allow the molecules to self-assemble into a lamellar nanostructure, and can offer reinforcement properties in solid inks that have heretofore not been explored.

In an embodiment, the present disclosure provides a hydrophobically- or hydrophilically-functionalized polyhedral oligomeric silsesquioxane, such as a functionalized polyhedral oligomeric silsesquioxane having the following formula:

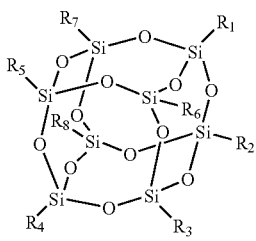

wherein each of the $R_1$ to $R_8$ groups can be the same or different, and independently represents a linear, branched or cyclic organic group that can be either a hydrophobic alkyl, aryl, arylalkyl, or cycloaliphatic group, alternatively an organic hydrophilic moiety, provided that at least one of the organic functional groups is a hydrophobic wax-like alkyl group.

In another embodiment, the present disclosure provides a method of making a functionalized polyhedral oligomeric silsesquioxane, comprising reacting a polyhedral oligomeric silsesquioxane starting material that contains at least one functional group that can be readily converted into one or more hydrophobic waxy aliphatic chains, with a suitable reagent to provide a wax-like aliphatic group at the reaction site.

In still another embodiment, the disclosure provides a nanostructure comprising a plurality of hydrophobically-functionalized polyhedral oligomeric silsesquioxane particles, arranged into a substantially lamellar structure.

In still another embodiment, the disclosure provides a solid phase change ink composition generally comprising at least a carrier and the above functionalized polyhedral oligomeric silsesquioxane.

EMBODIMENTS

Figure 1:
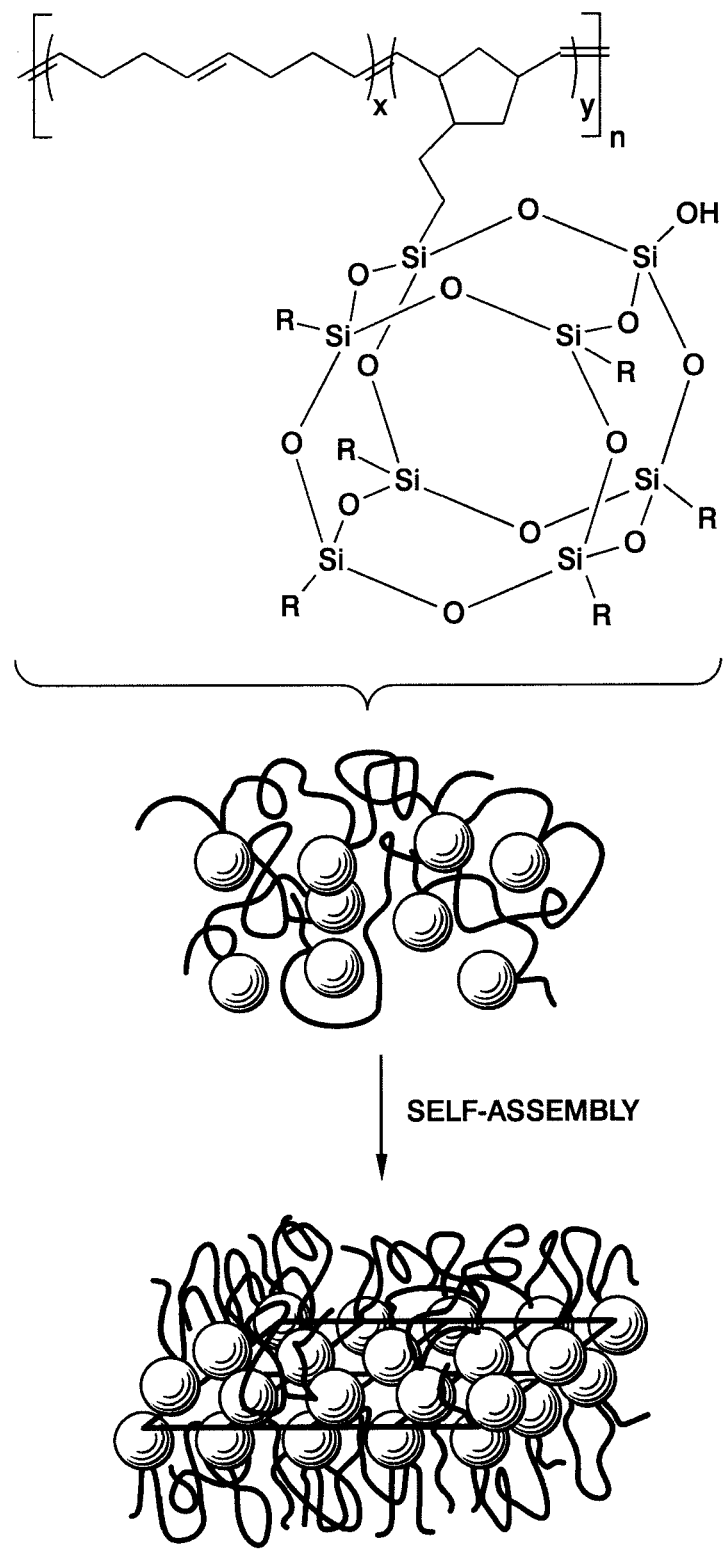
FIG. 1 depicts formation of a polybutadiene-POSS nanostructure.

Embodiments of the present disclosure provide nanostructured particles comprising hydrophobically-functionalized polyhedral oligomeric silsesquioxane. The hydrophobically-functionalized polyhedral oligomeric silsesquioxanes are generally represented by the following formula:

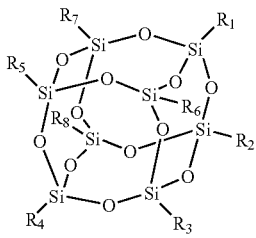

where each of the $R_1$ to $R_8$ groups, which can be the same or different, independently represent organic alkyl or cycloalkyl groups, such as substituted or unsubstituted aliphatic or aromatic hydrocarbon groups, such as having from one to about 50 carbon atoms, or from about 2 to about 30 carbon atoms, or from about 4 to about 18 carbon atoms. The hydrocarbon groups can be cyclic, branched or linear. The hydrocarbon groups can be saturated or may contain unsaturation. The hydrocarbon groups can be unsubstituted or substituted with one or more groups selected from the group consisting of halogen, methyl, ethyl, isobutyl, isooctyl, cyclopentyl, cyclohexyl, vinyl, styrl, trimethylsiloxyl, trichlorosilylethyl, trichlorosilylpropyl, dichlorosilylethyl, chlorosilylethyl, phenyl, chlorobenzyl, cyanoethyl, cyanopropyl, norbornenyl, fluoro, silanol, dimethylsilane, alkoxy, methacrylate, silane, aniline, amine, phenol, and alcohol. In certain embodiments, the hydrocarbon group is partially fluorinated or perfluorinated.

However, to provide the hydrophobically-functionalized polyhedral oligomeric silsesquioxanes, at least one of the $R_1$ to $R_8$ groups is a wax-like aliphatic group. The term "wax-like aliphatic group" refers, for example, to a long, hydrophobic chain having at least 10 or at least 12 or at least 16 carbon atoms, such as having from about 10 to about 100 or from about 12 to about 50 or from about 16 to about 40 carbon atoms. The wax-like aliphatic group can be a saturated alkane hydrocarbon, such as poly(alkylene) wax like polyethylene, polypropylene, and the like, or can be unsaturated hydrocarbon like polybutadiene, polyisoprene, and the like, or can be a short saturated alkane group, either linear, branched or containing cyclic groups, such as hexadecyl, octadecyl, eicosanyl, docosanyl, tetracosanyl, hexacosanyl, octacosanyl, triacontanyl, hexatriacontanyl, or larger and including mixtures thereof. The wax-like aliphatic group can also have multiple reactive functional groups for attachment to the POSS group. Examples of compounds having multiple reactive functional groups for attachment to POSS are the C-36 dimer diol, C-36 dimer diacid, or C-36 dimer diamine, which are commercial wax-like aliphatic compounds available from UNIQEMA® that contain either two alcohol, carboxylic acid, or amino functional groups, respectively, and are manufactured by dimerization of oleic acid derivatives. The wax-like aliphatic hydrocarbon can possess from 1 to about 10 reactive functional groups, such as 1 to about 6 reactive functional groups, or from 1 to about 4 reactive functional groups. The reactive functional R group on the POSS molecule can be used either for covalent grafting by way of known chemical transformations or as a POSS macromonomer for polymerization, and the reactive moiety in the R group can include: halogens (bromo, chloro, iodo, fluoro), primary or secondary hydroxyl, thiols, trialkoxysilyl, alkyldialkoxysilyl, dialkylalkoxysilyl, chlorodialkylsilyl, chlorodialkylsilyl, chlorodialkoxysilyl, dichloroalkylsilyl, trichlorosilyl, trivinylsilyl, dialkylvinylsilyl, dialkylsilanyl, trialkylsilanol, primary or secondary alkoxyl, carboxylic acid or anhydride, alkoxycarbonyl ester, alkoxythiocarbonyl ester, thiol ester, primary or secondary amides, isocyanato, isothiocyanato, nitrile, epoxy or oxirane groups such as glycidyl ethers, alkenyl groups and ethylenically unsaturated groups such as (meth)acrylate, vinyl ether, terminal olefin such as allyl, norbornenyl, cyclohexenyl or styryl, aldehyde or ketone, substituted amine, substituted imine, guanidino, substituted ammonium and/or phosphonium cation, carbamate or urethane, ureas, hydrazine, and semicarbazide.

The wax-like aliphatic group is desirably hydrophobic, relative to the polyhedral oligomeric silsesquioxane (POSS) group or moiety. Thus, for example, since the wax-like aliphatic group is more hydrophobic that the POSS moiety, then the hydrophobically-functionalized POSS compound has a wax-like aliphatic group that functions as a hydrophobic "tail" group, and the POSS moiety functions as a polar "head" group. This bipolar functionality enables the self-assembly of multiple hydrophobically-functionalized POSS molecules, as desired.

The ratio of POSS moieties to wax-like aliphatic groups can be adjusted, as desired. Thus, while at least one of the $R_1$ to $R_8$ groups is a wax-like aliphatic group, the ratio can be adjusted to provide several wax-like aliphatic group substitutions of the polyhedral oligomeric silsesquioxane compound. In embodiments, the ratio of POSS moieties to wax-like aliphatic groups can be adjusted, for example, from about 1:1, which provides a compound where only one of the groups is a wax-like aliphatic group, to about 1:8, which provides a compound where all or nearly all of the $R_1$ to $R_8$ groups are wax-like aliphatic groups. Thus, in embodiments, the ratio of POSS moieties to wax-like aliphatic groups can be from about 1:1 to about 1:4 or about 1:8, such as about 1:1, about 1:2. In still other embodiments, for example, one can form dimeric or multimeric hydrophobically-functionalized polyhedral oligomeric silsesquioxane compounds by using a wax-like aliphatic group that has two or more reactive functional groups for covalent bonding to the POSS moiety. The ratio of POSS moieties to wax-like aliphatic groups can be adjusted so that there are two or more POSS moieties attached to any one wax-like aliphatic group, for example a ratio of about 2:1 can be obtained when wax-like aliphatic group that is difunctional), or a ratio of about 3:1 can be obtained when the wax-like aliphatic group is trifunctional, and the like.

The hydrophobically-functionalized polyhedral oligomeric silsesquioxanes of the disclosure can be readily prepared from commercially available materials using conventional chemical synthesis. For example, the synthesis can begin with a commercially available polyhedral oligomeric silsesquioxanes compound, such as those available from Hybrid Plastics (Hattiesburg, Miss.) that contains at least one reactive functional group that can be readily converted into one or more waxy aliphatic chains through known chemical transformations. For example, at least one reactive functional group on the polyhedral oligomeric silsesquioxanes compound raw material can be an ester, an alcohol, an amine, isocyanate, or those described in embodiments. This reactive functional group can then be readily transformed and extended into a wax-like aliphatic group by reaction with a suitable reagent, such as a saturated or unsaturated hydrocarbon monocarboxylic or dicarboxylic acid, a saturated or unsaturated hydrocarbon ester or diester, a saturated or unsaturated hydrocarbon isocyanate or diisocyanate, a saturated or unsaturated hydrocarbon amine or diamine, a saturated or unsaturated hydrocarbon alcohol or diol, or other reactive functional groups attached to saturated or unsaturated hydrocarbons.

Specific suitable examples of reagents that can be used include monofunctional waxes such as (a) saturated hydrocarbon monocarboxylic acids wherein the number of carbon atoms (n) can range from about 12 to about 100, such as hexadecanoic or palmitic acid with n=16, heptadecanoic with n=17, octadecanoic or stearic acid with n=18, eicosanoic or arachidic (arachidonic) acid with n=20, docosanoic or behenic acid with n=22, tetracosanoic or lignoceric acid with n=24, hexacosanoic or cerotic acid with n=26, heptacosanoic with n=27, octacosanoic or montanic acid with n=28, triacontanoic with n=30, dotriacontanoic with n=32, tritriacontanoic, with n=33, tetratriacontanoic with n=34, pentatriacontanoic with n=35, or mixtures of long chain saturated carboxylic acids such as the Unicid® waxes from Baker-Petrolite that have greater than 30 carbon atoms; (b) unsaturated monocarboxylic acid waxes, such as oleic, linoleic, erucic and the like, (c) branched saturated or unsaturated monocarboxylic acid waxes, for example compounds known as the Guerbet acids such as 2-decyltetradecanoic acid (obtained as Jaric I-24 from Jarchem Industries, Newark, N.J.), isostearic acid, and ISOCARB® 32 from Sasol North America (Houston, Tex.); (d) saturated hydrocarbon alcohols wherein the number of carbon atoms (n) can range from about 12 to about 100, such as dodecanol with n=12, tetradecanol with n=14, hexadecanol with n=16, octadecanol (or, stearyl alcohol) with n=18, isostearyl alcohol with n=18, eicosanol with n=20, docosanol with n=22, tetracosanol with n=24, and the UNILIN® mixture of linear primary alcohols with n=24 to 50 carbons that are commercially available from Baker-Petrolite (Sugar Land, Tex.) or the ALFOL® blends of saturated primary alcohols with n>20 commercially available from Sasol North America (Houston, Tex.); (e) linear unsaturated primary alcohols such as hexadecenyl alcohol with n=16, octadecenyl alcohol (oleyl alcohol) with n=18, linoleyl alcohol with n=18 and the like; (f) branched saturated primary alcohols such as iso-stearyl alcohol or the Guerbet-type alcohols such as 2-hexyldecanol with n=16, or iso-arachidyl alcohol with n=20, or 2-tetradecyloctadecanol with n=32 (available from Jarchem Industries, Newark, N.J.), or the ISOFOL® series of branched primary alcohols with n=18 available from Sasol North America (Houston, Tex.); or the $C_{36}$-dimer diol mixtures with n=36 that have a main component being 10,11-dioctyleicosanediol such as commercial materials such as Pripol 2003 or Pripol 2033 available from Uniqema (New Castle, Del.); (g) saturated hydrocarbon amines wherein the number of carbon atoms (n) can range from about 12 to about 100, such as dodecylamine, octadecylamine (stearylamine) and similar aliphatic amines, or primary ether amines prepared from fatty alcohols and propylamine units such as tetradecyl-dodecyloxypropylamine obtained commercially as PA-1816 (Tomah Products, Milton, Wis.); (h) branched saturated primary amines such as isostearylamine or branched saturated ether amines such as 3-aminopropylether-functionalized branched alcohols obtained from Tomah Products (Milton, Wis.); and (i) other monofunctional hydrocarbon waxes with the same hydrocarbon structure as listed above in (a) to (h) and wherein the functional group is a carboxylic acid derivative such as an ester, amide, anhydride, urethane or carbamate, urea or isocyanate. Suitable examples of these types of reagents are stearyl isocyanate, $C_{36}$-dimer diisocyanate available from Uniqema (New Castle, Del.), methyl oleate, methyl stearate, methyl octacosanoate (montanic acid methyl ester), and lauryl palmitoleate; and any mixtures thereof of reagents listed above in (a) to (i).

Other examples of suitable reagents that can be used include difunctional hydrocarbon waxes, such as (a) linear or branched dicarboxylic acids wherein the number of carbon atoms (n) can range from about 12 to about 100, such as 1,12-dodecanedioic acid with n=12, 1,15-pentadecanedioic acid with n=15, 1,18-octadecanedioic acid with n=18, and 8-oxo-pentadecanedioic acid with n=15 (available from Fulcrum Scientific, Huddersfield, UK), 1,18-octadecanedioic acid with n=20 (available from TCI America Organic Chemicals, Portland, Oreg.), docosanedioic acid with n=22 (available from Aldrich, Milwaukee, Wis.) and $C_{36}$-dimer diacid mixtures with n=36 and having main component being 10,11-dioctyleicosanedioic acid such as commercial materials Pripol 1006 or Pripol 1009 (available from Uniqema, New Castle, Del.); and (b) linear or branched primary diols wherein the number of carbon atoms (n) can range from about 12 to about 100, such as 1,18-octadecanediol or 1,18 Octadec-9-en-diol (available commercially as, respectively, as D18 and D18U from Jarchem Industries, Newark, N.J.) or the $C_{36}$-dimer diol mixtures with n=36 that have a main component being 10,11-dioctyleicosanediol such as commercial materials such as Pripol 2003 or Pripol 2033 available from Uniqema (New Castle, Del.); and (c) linear or branched primary diamines wherein the number of carbon atoms (n) can range from about 12 to about 100, such as $C_{36}$-dimer diamines such as Versamine 552 (saturated) or Versamine 551 (unsaturated) obtained from Henkel (presently Cognis), or the JEFFAMINE series of polyether diamines based on a polyethylene glycol backbone (available from Huntsman, Woodlands, Tex.); and any mixtures thereof of reagents listed above in (a) to (c).

As will be apparent, the range of suitable chemical functional groups on the polyhedral oligomeric silsesquioxanes compound raw material is large, although the chemical functional group in embodiments contains at least 12 carbons, such as from about 12 to about 100 carbon atoms, and may optionally include one or more hetero atoms such as O, N, S or P or halogen atoms such as F, Cl, Br, and I.

If desired or necessary, the reaction can be conducted in the presence of a catalyst. When a catalyst is used, any suitable catalyst can be used in known amounts. In general, where the catalyst is an acid catalyst, it is desirably used in an amount of 10 mole % or less based on the amount of starting POSS material, since POSS compounds can hydrolyze with high levels of strong acid catalysts. However, where higher amounts of catalyst are used, the catalyst can be present in an amount of less than 50 mol % catalyst, such as less than 25 mol % catalyst. However the amount of catalyst used can also be outside these ranges.

In another embodiment, the functional group attached to the POSS compound is a hydrophilic group. Suitable hydrophilic groups include, for example, acid polar groups such as carboxylic acid and derivatives groups, sulfonic acid and derivatives groups, phosphoric acid and derivatives groups and formyl groups; basic polar groups such as amino groups; and neutral polar groups such as amide groups, ester groups, hydroxyl groups, alkoxyl groups, halo groups, and nitrile groups. Of course, other hydrophilic groups can be used, as well as combinations thereof. The hydrophilic groups can be incorporated into the POSS structure in any suitable manner, using commonly known chemical transformations.

Although not limited by any particular theory, it is believed that POSS is an organosilicate compound with a cage-like chemical structure that assumes a nearly spherical shape, and when functionalized with a long aliphatic/hydrophobic carbon chain, possesses a structure that resembles a non-ionic surfactant. These structural features of the wax-functionalized POSS can allow the molecules to self-assemble into a lamellar nanostructure, and are good examples of a class of highly ordered nanomaterials.

A benefit of the hydrophobically-functionalized polyhedral oligomeric silsesquioxanes of the disclosure is that they can readily self-assemble into nanostructures, such as substantially lamellar nanostructures, with dimensions in the region of about 1 to about 500 nm, such as about 1 to about 300 nm or about 1 to about 100 or to about 200 nm.

Figure 2:
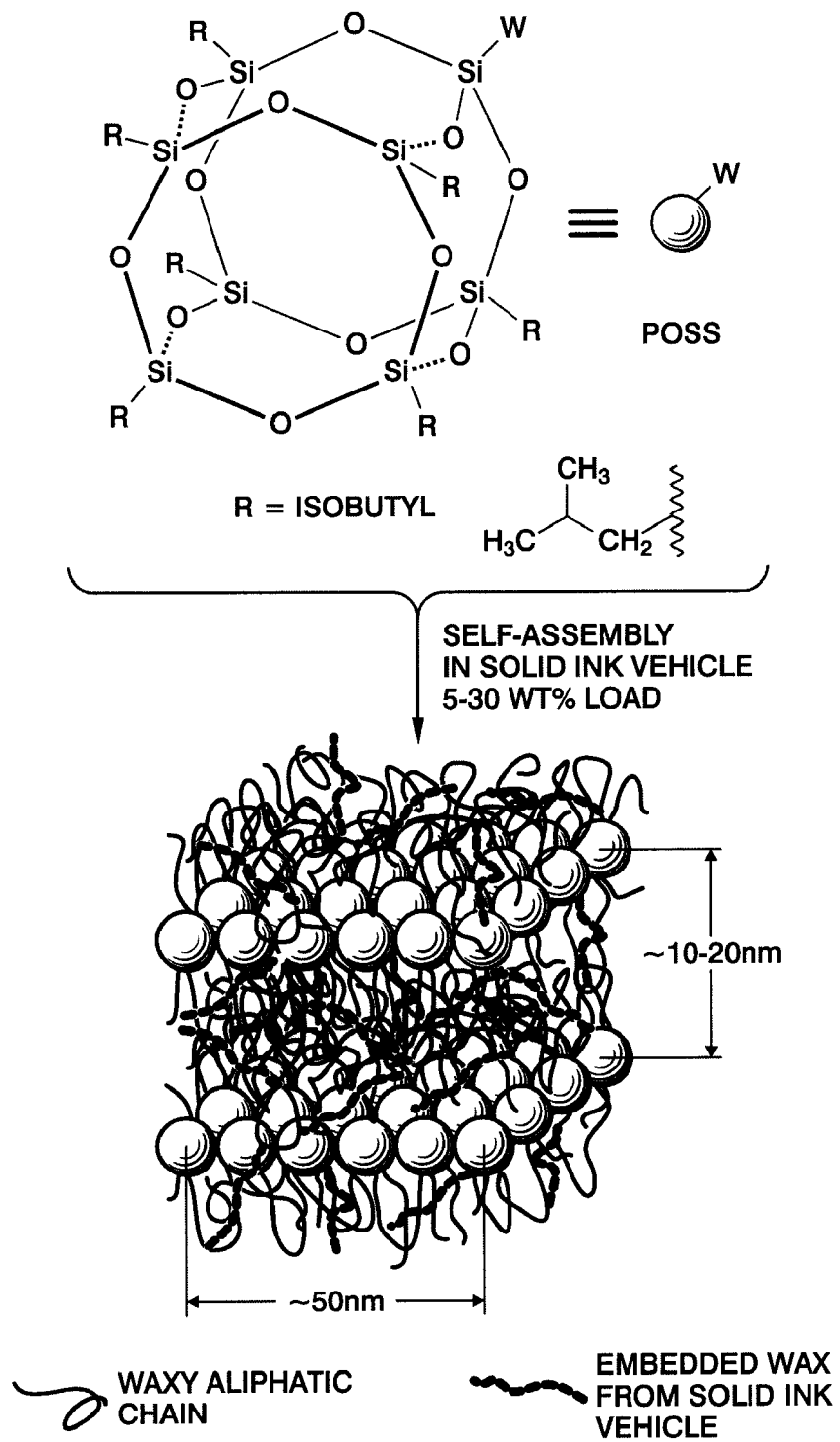
FIG. 2 depicts a self-assembly of hydrophobically-functionalized polyhedral oligomeric silsesquioxanes into substantially lamellar nanostructures.

The self-assembly of the hydrophobically-functionalized polyhedral oligomeric silsesquioxanes into substantially lamellar nanostructures is depicted in FIG. 2. FIG. 2 illustrates the proposed nanostructured wax-functionalized POSS material. FIG. 2 also shows how this lamellar nanostructure can interact with wax components in a composition such as a solid ink, where wax components of the solid ink vehicle can occupy the interstitial spaces of the nanostructure where the hydrophobic alkyl chains reside.

Based on small-angle X-ray scattering (SAXS) data measured by Zheng et al. cited above, for nanostructures built from PBD-functionalized POSS, the distance between lamellae sheets formed from the hydrophobically-functionalized polyhedral oligomeric silsesquioxanes of the present disclosure is expected to be in the range of 10-20 nm. Thus, in embodiments, the distance between lamellae sheets can be from about 1 to about 100 nm, such as from about 2 to about 80 nm or about 10 to about 50 nm The lateral dimensions of the nanostructure, as well as the potential stacking of lamellar sheets within an array, can be controlled by the weight-percent loading of the wax-modified POSS particles within a desired composition such as a wax-based ink vehicle. In embodiments, the loading of wax-modified POSS particles in a desired composition can be about 1 wt % or less to about 50 wt % or more. In some applications, such as solid ink vehicles, the wax-modified POSS particles can be present in a loading range of about 1 to about 50 wt %, such as no more than about 25 wt % within the ink, or no greater than about 15 wt % in the ink.

The formed lamellar nanostructures can be used, for example, as reinforcing agents in a variety of compositions, such as in liquid ink vehicles. For example, the hydrophobically-functionalized POSS nanoparticles can be formulated into a variety of ink vehicles, including "low energy" solid inks or phase-change inks with melt temperatures that range from about 60 to about 130° C., solvent-based liquid inks or radiation-curable liquid inks comprised of alkyloxylated monomers, and even aqueous inks. For end-use application in piezoelectric inkjet printing, nanosized pigment particles are advantageous to ensure reliable inkjet printing and prevent blockage of jets due to pigment particle agglomeration. Various of such compositions will now be described in more detail.

Ink jet ink compositions according to this disclosure generally include a carrier, a colorant, and one or more additional additives. Such additives can include, for example, solvents, waxes, functional resins, particle dispersing agents, antioxidants, tackifiers, slip aids, curable components such as curable monomers and/or polymers, gellants, initiators, sensitizers, humectants, biocides, preservatives, and the like. Specific types and amounts of components will depend, of course, on the specific type of ink composition, such as liquid, curable, solid, hot melt, phase change, gel, or the like. The formed lamellar nanostructures can be used, for example, in such inks as reinforcing agents. The reinforcing action of the POSS nanostructures may also be further enhanced with the use of organogelators or gellant components, which act to form crystallizing 2-dimensional networks within the ink carrier that may assist with alignment or co-crystallization of the POSS nanostructured particles.

The ink composition also includes a carrier material, or mixture of two or more carrier materials. The carrier material can vary, for example, depending upon the specific type of ink composition. In the case of a solid (or phase change) ink jet ink composition, the carrier can include one or more organic compounds. The carrier for such solid ink compositions is typically solid at room temperature (about 20° C. to about 25° C.), but undergoes a phase change to become liquid at the printer operating temperature required for ejecting onto the print surface, which can range from about 60° C. to about 140° C., but can also be outside that range. The ink carrier disclosed herein can contain a low-melting wax, which can be comprised of a polyalkylene wax, such as polyethylene or polypropylene waxes or mixtures thereof. The polyalkylene wax(es) can be present in the ink carrier in any desired or effective amount, in one embodiment of at least about 25% by weight of the ink carrier, in another embodiment of at least 30% by weight of ink carrier, and in yet another embodiment of at least about 35% by weight of the ink carrier, and in one embodiment equal to or less than about 65% by weight of the ink carrier, in another embodiment equal to or less than about 55% by weight of the ink carrier, and in yet another embodiment equal to or less than about 50% by weight of the ink carrier, although the amount can be outside of these ranges.

Examples of suitable polyalkylene waxes include POLY-WAX® 500 and distilled POLYWAX® 500 (available from Baker Petrolite), POLYWAX® 400 and distilled POLY-WAX® 400 (available from Baker Petrolite), VYBAR® 103 and VYBAR® 253 (available from Baker Petrolite), and POLYWAX® 655. Higher molecular weight POLYWAX® materials are also suitable. The molecular weight of the polyalkylene wax is in an embodiment of this disclosure in the range of 500 to 600 g/mole with a polydispersity equal to or less than about 1.1.

Additional suitable solid ink carrier materials include paraffins, microcrystalline waxes, ester waxes, amide waxes, fatty acids, fatty alcohols, fatty amides and other waxy materials, sulfonamide materials, resinous materials made from different natural sources (such as, for example, tall oil rosins and rosin esters), and many synthetic resins, oligomers, polymers and copolymers, such as ethylene/vinyl acetate copolymers, ethylene/acrylic acid copolymers, ethylene/vinyl acetate/acrylic acid copolymers, copolymers of acrylic acid with polyamides, and the like, ionomers, and the like, as well as mixtures thereof. One or more of these materials can also be employed in a mixture with a fatty amide material and/or an isocyanate-derived material. Further, these waxes can be used in addition to the formed lamellar nanostructures, if desired.

Suitable carrier materials for solid ink compositions can thus also include, for example, amides, including diamides, triamides, tetra-amides, and the like. Suitable triamides include, for example, those disclosed in U.S. Patent Publication No. 2004-0261656, the entire disclosure of which is incorporated herein by reference. Suitable other amides, such as fatty amides including monoamides, tetra-amides, mixtures thereof, are disclosed in, for example, U.S. Pat. Nos. 4,889,560, 4,889,761, 5,194,638, 4,830,671, 6,174,937, 5,372,852, 5,597,856, and 6,174,937, and British Patent No. GB 2 238 792, the entire disclosures of each are incorporated herein by reference. In embodiments where an amide is used as a carrier material, a triamide is particularly useful because triamides are believed to have structures that are more three-dimensional as compared to other amides such as diamides and tetraamides. For example, the ink carrier may contain a branched tetra-amide such as those described in U.S. Pat. No. 6,174,937, the disclosure of which is totally included here by reference, wherein n is an integer greater than or equal to 39 and less than 99; and wherein $R_1$ and $R_2$ each comprise at least one carbon unit.

The ink carrier may also contain a branched triamide such as those described in U.S. Pat. No. 6,860,930, the disclosure of which is totally included here by reference, wherein n has an average value of from about 34 equal to or less than 40, where x, y, and z can each be zero or an integer, and wherein the sum of x, y, and z is from about 5 and equal to or less than 6.

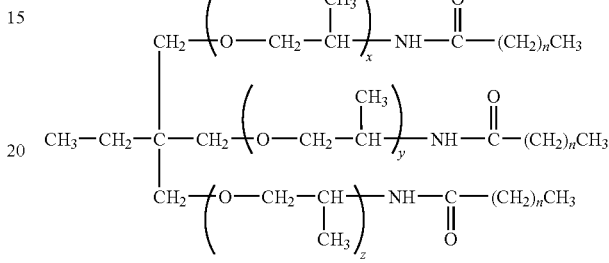

The ink carrier may also include a gelling agent (gellant), which can be a crystalline or semi-crystalline material. Suitable examples of gellants for use in the ink carrier of phase change ink compositions include, but are not limited to, ester-terminated amide gellants such as UNI-REZ® 2980 and UNICLEAR® 100 (commercially available from Arizona Chemical, Jacksonville, Fla.) and the like, as well as ester-amide gellants such as those disclosed in, for example, U.S. Pat. Nos. 5,863,317, 5,645,632, and 5,783,657, the disclosures of each of which are totally incorporated herein by reference. The ester-amide gellant can be present in the ink carrier in any desired or effective amount that ranges from about 0.5% to about 30% by weight of the ink carrier, although the amount can be outside of these ranges.

Other suitable gellants for use in phase change ink compositions can include urea or urethane type of gelating agents, such as N,N-dialkyl urea compounds or N,O-dialkyl carbamate compounds, or urea-urethane compounds as well as dimeric urea-urethane compounds including trans-1,2-cyclohexane bis[urea-urethane] compounds such as those disclosed in U.S. Pat. Nos. 7,220,300, 7,144,450, 7,144,450 and U.S. Pat. Publication Nos. US 2006/0117992 A1, 2006/0122415 A1, and US 2006/0122416 A1, the disclosures of each of which are totally incorporated herein by reference, or mixtures thereof.

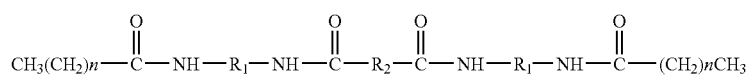

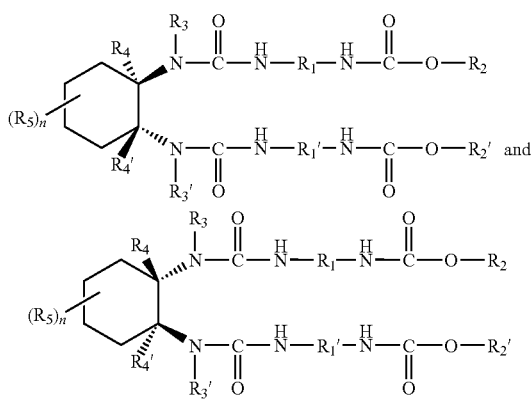

wherein $R_1$ and $R'_1$ each, independently of the other, is an alkylene group, an arylene group, an arylalkylene group, or an alkylarylene group, $R_2$ and $R'_2$ each, independently of the other, is an alkyl group, an aryl group, an arylalkyl group, or an alkylaryl group, $R_3$ and $R'_3$ each, independently of the other, is a hydrogen atom or an alkyl group, $R_4$ and $R'_4$ each, independently of the other, is a hydrogen atom, a fluorine atom, an alkyl group, or a phenyl group, n is an integer of 0, 1, 2, 3, or 4, and $R_5$ is an alkyl group, an aryl group, an arylalkyl group, an alkylaryl group, or a substituent other than an alkyl, aryl, arylalkyl, or alkylaryl group.

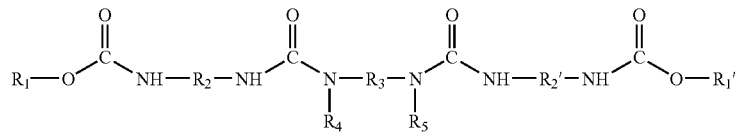

wherein $R_1$ and $R_{1'}$ each, independently of the other, is an alkyl group, an aryl group, an arylalkyl group, or an alkylaryl group, $R_2$ and $R_{2'}$ each, independently of the other, is an alkylene group, an arylene group, an arylalkylene group, or an alkylarylene group, $R_3$ is an alkylene group, an arylene group, an arylalkylene group, or an alkylarylene group, and $R_4$ and $R_5$ each, independently of the other, is a hydrogen atom or an alkyl group.

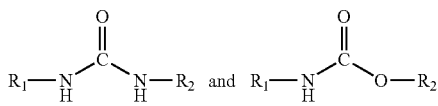

wherein $R_1$ and $R_2$ is each, independently of the other, (i) an alkyl group, including linear, branched, saturated, unsaturated, cyclic, substituted, and unsubstituted alkyl groups, and wherein hetero atoms, such as oxygen, nitrogen, sulfur, silicon, phosphorus, boron, and the like either may or may not be present in the alkyl group, and having at least 4 carbon atoms and not more than about 60 carbon atoms, although the number of carbon atoms can be outside of these ranges.

Gelling agent can have a melting point of at least about 60° C. and not more than about 160° C., although the melting point can be outside of this range. The gelling agent is present in the ink carrier in any desired or effective amount, in the range of at least about 0.5% by weight and not more than about 30% by weight, although the amount can be outside of these ranges.

Other suitable carrier materials that can be used in the solid ink compositions include, for example, isocyanate-derived resins and waxes, such as urethane isocyanate-derived materials, urea isocyanate-derived materials, urethane/urea isocyanate-derived materials, mixtures thereof, and the like.

The ink carrier in a solid ink composition can be present in ink in any desired or effective amount. For example, the carrier can be present in an amount of about 0.1 to about 99 percent by weight of the ink, such as about 50 to about 98 percent by weight of the ink, or about 90 to about 95 percent by weight of the ink, although the amount can be outside of these ranges.

The ink compositions can also optionally contain a viscosity modifier. Examples of suitable viscosity modifiers include aliphatic ketones, such as stearone, and the like. When present, the optional viscosity modifier can be present in the ink in any desired or effective amount, such as about 0.1 to about 99 percent by weight of the ink, such as about 1 to about 30 percent by weight of the ink, or about 10 to about 15 percent by weight of the ink, although the amount can be outside of these ranges.

Generally, the ink compositions contain one or more colorant. Any desired or effective colorant can be employed in the ink compositions, including pigment, dye, mixtures of pigment and dye, mixtures of pigments, mixtures of dyes, and the like. Examples of such conventional colorants include Color Index (C.I.) Solvent Dyes, Disperse Dyes, modified Acid and Direct Dyes, Basic Dyes, Sulphur Dyes, Vat Dyes, and the like. Examples of suitable dyes include Neozapon Red 492 (BASF); Orasol Red G (Ciba-Geigy); Direct Brilliant Pink B (Crompton & Knowles); Aizen Spilon Red C-BH (Hodogaya Chemical); Kayanol Red 3BL (Nippon Kayaku); Levanol Brilliant Red 3BW (Mobay Chemical); Levaderm Lemon Yellow (Mobay Chemical); Spirit Fast Yellow 3G; Aizen Spilon Yellow C-GNH (Hodogaya Chemical); Sirius Supra Yellow GD 167; Cartasol Brilliant Yellow 4GF (Sandoz); Pergasol Yellow CGP (Ciba-Geigy); Orasol Black RLP (Ciba-Geigy); Savinyl Black RLS (Sandoz); Dermacarbon 2GT (Sandoz); Pyrazol Black BG (ICI); Morfast Black Conc, A (Morton-Thiokol); Diaazol Black RN Quad (ICI); Orasol Blue GN (Ciba-Geigy); Savinyl Blue GLS (Sandoz); Luxol Blue MBSN (Morton-Thiokol); Sevron Blue 5GMF (ICI); Basacid Blue 750 (BASF), Neozapon Black $X_{51}$ (C.I. Solvent Black, C.I. 12195) (BASF), Sudan Blue 670 (C.I. 61554) (BASF), Sudan Yellow 146 (C.I. 12700) (BASF), Sudan Red 462 (C.I. 26050) (BASF), Intratherm Yellow 346 from Crompton and Knowles, C.I. Disperse Yellow 238, Neptune Red Base NB543 (BASF, C.I. Solvent Red 49), Neopen Blue FF-4012 from BASF, Lampronol Black BR from ICI (C.I. Solvent Black 35), Morton Morplas Magenta 36 (C.I. Solvent Red 172), metal phthalocyanine colorants such as those disclosed in U.S. Pat. No. 6,221,137, the disclosure of which is totally incorporated herein by reference, and the like. Polymeric dyes can also be used, such as those disclosed in, for example, U.S. Pat. Nos. 5,621,022 and 5,231,135, the disclosures of each of which are totally incorporated herein by reference, and commercially available from, for example, Milliken & Company as Milliken Ink Yellow 869, Milliken Ink Blue 92, Milliken Ink Red 357, Milliken Ink Yellow 1800, Milliken Ink Black 8915-67, uncut Reactant Orange X-38, uncut Reactant Blue X-17, Solvent Yellow 162, Acid Red 52, Solvent Blue 44, and uncut Reactant Violet X-80.

Pigments are also suitable additional colorants for the ink compositions. Examples of suitable pigments include Violet Toner VT-8015 (Paul Uhlich); Paliogen Violet 5100 (BASF); Paliogen Violet 5890 (BASF); Permanent Violet VT 2645 (Paul Uhlich); Heliogen Green L8730 (BASF); Argyle Green XP-111-S (Paul Uhlich); Brilliant Green Toner GR 0991 (Paul Uhlich); Lithol Scarlet D3700 (BASF); Toluidine Red (Aldrich); Scarlet for Thermoplast NSD PS PA (Ugine Kuhlmann of Canada); E.D. Toluidine Red (Aldrich); Lithol Rubine Toner (Paul Uhlich); Lithol Scarlet 4440 (BASF); Bon Red C (Dominion Color Company); Royal Brilliant Red RD-8192 (Paul Uhlich); Oracet Pink RF (Ciba-Geigy); Paliogen Red 3871 K (BASF); Paliogen Red 3340 (BASF); Lithol Fast Scarlet L4300 (BASF); Heliogen Blue L6900, L7020 (BASF); Heliogen Blue K6902, K6910 (BASF); Heliogen Blue D6840, D7080 (BASF); Sudan Blue OS (BASF); Neopen Blue FF4012 (BASF); PV Fast Blue B2G01 (American Hoechst); Irgalite Blue BCA (Ciba-Geigy); Paliogen Blue 6470 (BASF); Sudan III (Red Orange) (Matheson, Colemen Bell); Sudan II (Orange) (Matheson, Colemen Bell); Sudan Orange G (Aldrich), Sudan Orange 220 (BASF); Paliogen Orange 3040 (BASF); Ortho Orange OR 2673 (Paul Uhlich); Paliogen Yellow 152, 1560 (BASF); Lithol Fast Yellow 0991 K (BASF); Paliotol Yellow 1840 (BASF); Novoperm Yellow FGL (Hoechst); Permanent Yellow YE 0305 (Paul Uhlich); Lumogen Yellow D0790 (BASF); Suco-Yellow L1250 (BASF); Suco-Yellow D1355 (BASF); Suco Fast Yellow D1355, D1351 (BASF); Hostaperm Pink E (American Hoechst); Fanal Pink D4830 (BASF); Cinquasia Magenta (Du Pont); Paliogen Black L0084 (BASF); Pigment Black K801 (BASF); and carbon blacks such as REGAL 330® (Cabot), Carbon Black 5250, Carbon Black 5750 (Columbia Chemical), and the like.

Other ink colors besides the subtractive primary colors can be desirable for applications such as postal marking or industrial marking and labeling using, for example, phase change printing, and the present disclosure is applicable to these needs. Further, infrared (IR) or ultraviolet (UV) absorbing dyes can also be incorporated into the ink compositions for use in applications such as "invisible" coding or marking of products. Examples of such infrared and ultraviolet absorbing dyes are disclosed in, for example, U.S. Pat. Nos. 5,378,574, 5,146,087, 5,145,518, 5,543,177, 5,225,900, 5,301,044, 5,286,286, 5,275,647, 5,208,630, 5,202,265, 5,271,764, 5,256,193, 5,385,803, and 5,554,480, the disclosures of each of which are totally incorporated herein by reference.

The colorant can be present in the ink composition in any desired or effective amount to obtain the desired color or hue. For example, the colorant can typically be present in an amount of at least about 0.1 percent by weight of the ink, such as at least about 0.2 percent by weight of the ink or at least about 0.5 percent by weight of the ink, and typically no more than about 50 percent by weight of the ink, such as no more than about 20 percent by weight of the ink or no more than about 10 percent by weight of the ink, although the amount can be outside of these ranges.

The ink compositions can also optionally contain an antioxidant. The optional antioxidants of the ink compositions protect the images from oxidation and also protect the ink components from oxidation during the heating portion of the ink preparation process. Specific examples of suitable antioxidants include NAUGUARD® series of antioxidants, such as NAUGUARD® 445, NAUGUARD® 524, NAUGUARD® 76, and NAUGUARD® 512 (commercially available from Uniroyal Chemical Company, Oxford, Conn.), the IRGANOX® series of antioxidants such as IRGANOX® 1010 (commercially available from Ciba Geigy), and the like. When present, the optional antioxidant can be present in the ink in any desired or effective amount, such as in an amount of from at least about 0.01 to about 20 percent by weight of the ink, such as about 0.1 to about 5 percent by weight of the ink, or from about 1 to about 3 percent by weight of the ink, although the amount can be outside of these ranges.

Other optional additives to the inks include clarifiers, such as UNION CAMP® X37-523-235 (commercially available from Union Camp); tackifiers, such as FORAL® 85, a glycerol ester of hydrogenated abietic (rosin) acid (commercially available from Hercules), FORAL® 105, a pentaerythritol ester of hydroabietic (rosin) acid (commercially available from Hercules), CELLOLYN® 21, a hydroabietic (rosin) alcohol ester of phthalic acid (commercially available from Hercules), ARAKAWA KE-311 Resin, a triglyceride of hydrogenated abietic (rosin) acid (commercially available from Arakawa Chemical Industries, Ltd.), synthetic polyterpene resins such as NEVTAC® 2300, NEVTAC® 100, and NEVTAC® 80 (commercially available from Neville Chemical Company), WINGTACK® 86, a modified synthetic polyterpene resin (commercially available from Goodyear), and the like; adhesives, such as VERSAMID® 757, 759, or 744 (commercially available from Henkel), plasticizers, such as UNIPLEX® 250 (commercially available from Uniplex), the phthalate ester plasticizers commercially available from Monsanto under the trade name SANTICIZER®, such as dioctyl phthalate, diundecyl phthalate, alkylbenzyl phthalate (SANTICIZER® 278), triphenyl phosphate (commercially available from Monsanto), KP-140®, a tributoxyethyl phosphate (commercially available from FMC Corporation), MORFLEX® 150, a dicyclohexyl phthalate (commercially available from Morflex Chemical Company Inc.), trioctyl trimellitate (commercially available from Eastman Kodak Co.), and the like; and the like. Such additives can be included in conventional amounts for their usual purposes.

A particle dispersing agent, or dispersant, can be present in the ink in any desired or effective amount for purposes of dispersing and stabilizing the wax-functionalized POSS nanostructures, or pigment particles (if present) or other nanoparticles present in the ink vehicle. The dispersant is present in any desired or effective amount ranging from at least $1\times10^{-3}\%$ by weight of the ink carrier, and not more than about 30% by weight of the ink carrier, although the amount can be outside of these ranges. Examples of suitable dispersants include, but are not limited to, polymeric binders that aid in the dispersion and coating ability of nanostructured particles in phase-change ink formulations include, such as derivatives of rosin natural products (tall oil, pine and other wood resins), acrylic-based polymers, styrene-based copolymers, copolymers of $\alpha$-olefins such as 1-hexadecene, 1-octadecene, 1-eicosene, 1-triacontene and the like, copolymers of vinyl pyridine, vinyl imidazole, and vinyl pyrrolidinone, polyester copolymers, polyamide copolymers, copolymers of acetals. Specific examples of polymeric binders include, but are not limited to, poly(vinyl butyral-co-vinyl alcohol-co-vinyl acetate), poly(vinyl acetate), poly(acrylic acid), poly (methacrylic acid), poly(vinyl alcohol), poly(methyl methacrylate), polyester, Lexan®, polycarbonate, poly(styreneb-4-vinylpyridine) and the like. Another class of suitable dispersants are polyalkylene succinimide dispersants such as those disclosed in U.S. Pat. No. 6,858,070, the disclosure of which is totally incorporated herein by reference. Dispersants can include the Chevron Oronite OLOA 11000, OLOA 11001, OLOA 11002, OLOA 11005, OLOA 371, OLOA 375, OLOA 411, OLOA 4500, OLOA 4600, OLOA 8800, OLOA 8900, OLOA 9000, OLOA 9200 and the like, commercially available from Chevron Oronite Company LLC, Houston, Tex., as well as mixtures thereof. Examples of suitable polyalkylene succinimides and their precursors and methods of making them are disclosed in, for example, U.S. Pat. Nos. 3,172,892, 3,202,678, 3,280,034, 3,442,808, 3,361,673, 3,172,892, 3,912,764, 5,286,799, 5,319,030, 3,219,666, 3,381,022, 4,234,435, and European Patent Publication 0 776 963, the disclosures of each of which are totally incorporated herein by reference.

A rosin ester resin, mixtures thereof, or the like can also be included in the ink carrier. The rosin ester resin is present in the ink carrier in any desired or effective amount, in one embodiment of at least about 0.5% by weight of the ink carrier, in another embodiment of at least about 2% by weight of the ink carrier, and in yet another embodiment of at least about 3% by weight of the ink carrier, and in one embodiment of equal to or less than about 20% by weight of the ink carrier, in another embodiment equal to or less than about 15% by weight of the ink carrier, and in yet another embodiment equal to or less than about 10% by weight of the ink carrier, although the amount can be outside of these ranges. Examples of suitable rosin ester resins include PINECRYSTAL® KE-100 (commercially available from Arakawa), and the like.

The solid or phase change ink compositions typically have melting points no lower than about 50° C., such as about 50° C. to about 160° C. or more. In embodiments, the ink compositions have a melting point of about 70° C. to about 140° C., such as about 80° C. to about 100° C., although the melting point can be outside of these ranges. The ink compositions also generally a have melt viscosity at the jetting temperature (such as typically about 75° C. to about 180° C., or about 100° C. to about 150° C. or about 120° C. to about 130° C., although the jetting temperature can be outside of these ranges) typically of about 2 to about 30 centipoise, such as about 5 to about 20 centipoise or about 7 to about 15 centipoise, although the melt viscosity can be outside of these ranges. Because image hardness tends to drop with lower viscosities, it is desired in embodiments that the viscosity be as low as possible while still retaining the desired degree of image hardness.

The ink compositions of the present disclosure can also optionally contain other materials, which may depend upon the type of printer in which the ink is used. For example, the carrier composition is typically designed for use in either a direct printing mode or an indirect or offset printing transfer system.

In other embodiments encompassing non-aqueous inks, the wax-functionalized POSS nanoparticles can be used in solvent-borne inks such as petroleum-based inks which can include aliphatic hydrocarbons, aromatic hydrocarbons, and mixtures thereof, environmentally friendly soy and vegetable oil-based inks, linseed oil-based inks and other ink-based vehicles derived from natural sources. Other examples of ink vehicles for the wax-functionalized POSS nanoparticles include isophthalic alkyds, higher order alcohols and the like. In still other embodiments, the present invention of the wax-functionalized POSS nanoparticles can be applied towards inks used in relief, gravure, stencil, and lithographic printing.

The ink compositions of the present disclosure can be prepared by any desired or suitable method. For example, in the case of solid or phase change inks, the ink ingredients can be mixed together, followed by heating, typically to a temperature of from about 100 to about 140° C., although the temperature can be outside of this range, and stirring until a homogeneous ink composition is obtained, followed by cooling the ink to ambient temperature (typically from about 20 to about 25° C.). In the case of liquid ink compositions, the ink ingredients can simply be mixed together with stirring to provide a homogeneous composition, although heating can also be used if desired or necessary to help form the composition.

The nanoparticles can, in an embodiment herein, be dispersed in a solvent, such as a low boiling solvent, and can then be transferred from the solvent phase to the ink vehicles where they are uniformly disseminated in the ink carrier and in the low energy phase change ink. The solvent can in one embodiment be an organic solvent, and in another embodiment be a low boiling organic solvent. These solvents in one embodiment have a boiling point of equal to or less than about 140° C., in another embodiment have a boiling point of equal to or less than about 130° C., and in a further embodiment have a boiling point equal to or less than about 120° C., although the boiling point can be outside of these ranges. The loading of wax-functionalized POSS nanoparticles in the solvent in one embodiment is at least about 10% by weight, in another embodiment is at least 20% by weight, and in a further embodiment is at least about 30% by weight, in one embodiment equal to or less than about 60 weight percent, in another embodiment equal to or less than about 50% by weight, and in a further embodiment equal to or less than about 45% by weight, although the loading can be outside of these ranges.

The inks disclosed herein can be obtained by dispersing the wax-functionalized POSS nanoparticle dispersions into the ink components in such a manner so as to maximize uniform dispersion and resist aggregation. For example, the method for producing a low energy phase change ink composition can involve combining together an ink carrier comprising a colloidal dispersion of wax-functionalized POSS nanoparticles in a solvent, a low melting wax, and optionally a gelling agent. The ink carrier exhibits a substantially uniform distribution of said nanoparticles discretely distributed therewithin, and exhibits a substantially increased resistance to aggregation of the nanoparticles distributed therewithin. The method can comprise combining the low melting wax and other components of the ink carrier such as the gelling agent, particle dispersant, resins and the like with the wax-functionalized POSS nanoparticles in a solvent while evaporating said solvent to form a substantially homogeneous solution of said ink carrier. Then, the colorant is added to the substantially homogeneous solution of the ink carrier to form the low energy phase change ink composition.

An example is set forth herein below and is illustrative of different compositions and conditions that can be utilized in practicing the disclosure. All proportions are by weight unless otherwise indicated. It will be apparent, however, that the disclosure can be practiced with many types of compositions and can have many different uses in accordance with the disclosure above and as pointed out hereinafter.

EXAMPLES

Example 1

Preparation of Wax-Functionalized POSS Nanoparticles

A mixture of [Ethyl Undecanoate]-Isobutyl-POSS (from Hybrid Plastics, 2.0 mmol, 2.06 grams), stearyl alcohol (4.0 mmol, 1.08 grams), and para-toluenesulfonic acid as catalyst (0.20 mmol, 0.04 grams) in 50 mL of toluene was heated to reflux for about 5 hours. The mixture was then cooled to room temperature, extracted into 100 mL ethyl acetate and washed with dilute sodium bicarbonate solution (10% $NaHCO_3$). The ethyl acetate extract was dried over anhydrous magnesium sulfate, filtered and concentrated to afford a transparent wax-like semi-solid in quantitative yield. $^1$H-NMR spectroscopy confirmed formation of the product. The reaction scheme is shown below.

Example 2

Preparation of Wax-Functionalized POSS Nanoparticles

A mixture of [Ethyl Undecanoate]-Isobutyl-POSS (from Hybrid Plastics, 4.12 grams, 4.0 mmol), a 36-carbon dimer diol known as Pripol 2003 purchased from Uniqema (2.0 mmol, 1.0 grams), and para-toluenesulfonic acid as catalyst (0.2 mmol, 0.04 grams) were added to 30 mL of toluene and heated to reflux for about 5 hours. The amber brown solution mixture was then cooled, extracted into 150 mL ethyl acetate and washed several times with deionized water to remove acid catalyst, then washed with brine solution until pH was neutral. The ethyl acetate extract was dried over anhydrous magnesium sulfate, filtered and concentrated to afford a dark yellow semi-solid paste in quantitative yield. $^1$H-NMR spectroscopic analysis determined the structure of the crude product as a mixture of mono-ester and di-ester products with no unreacted starting materials. The reaction scheme is shown below.

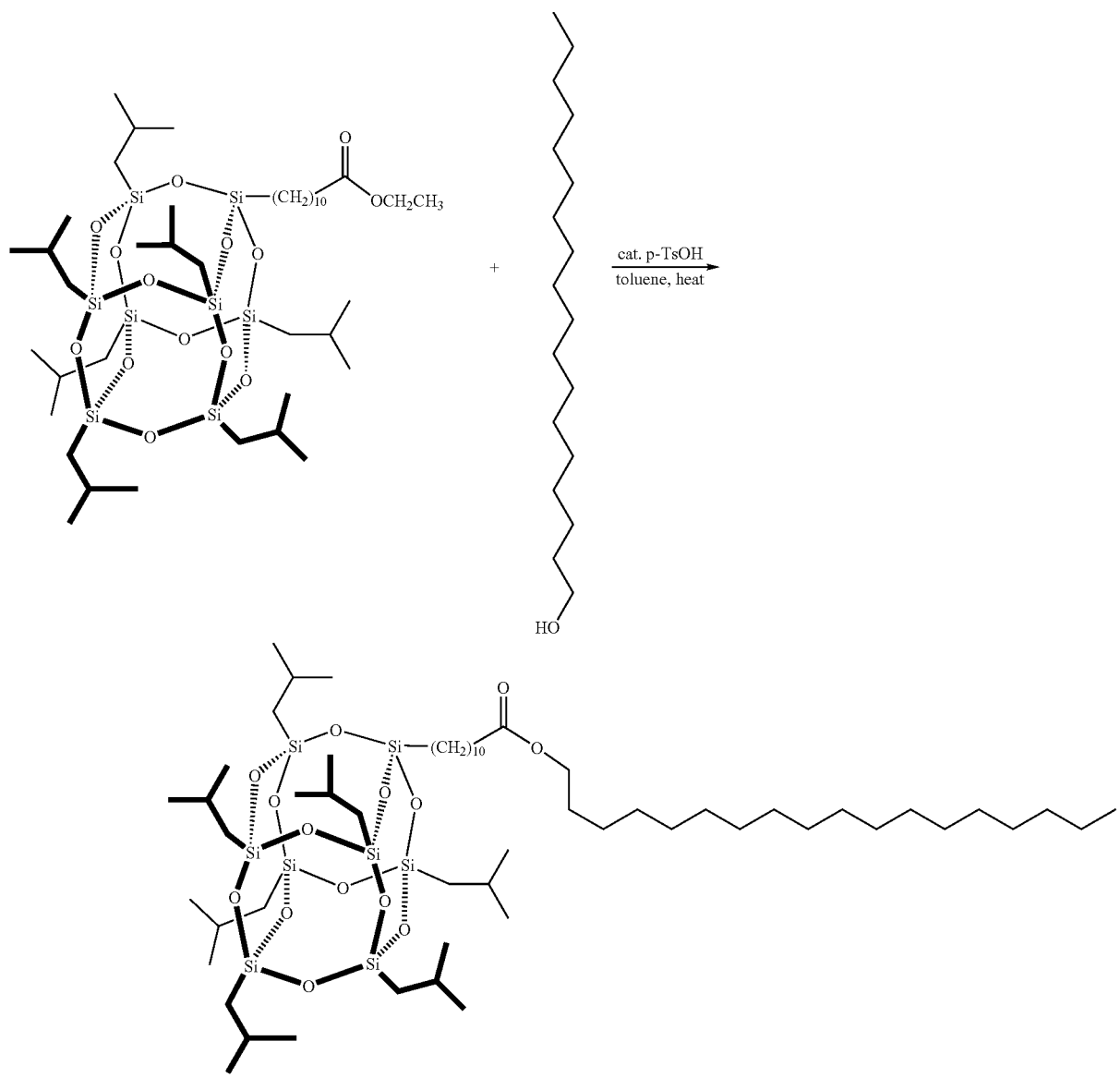

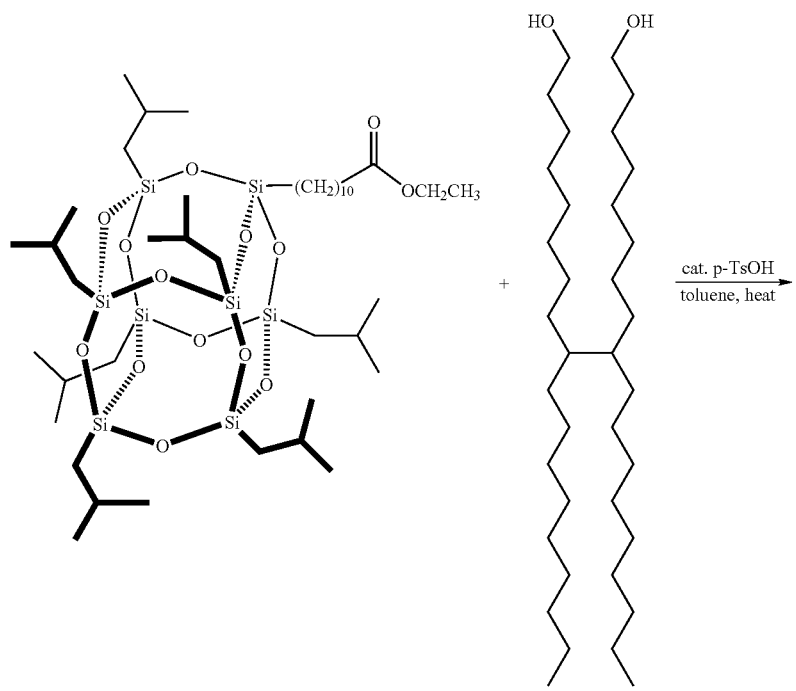
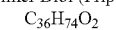
C-36 Dimer Diol (Pripol 2003)
$C_{36}H_{74}O_2$
MW = 538.97
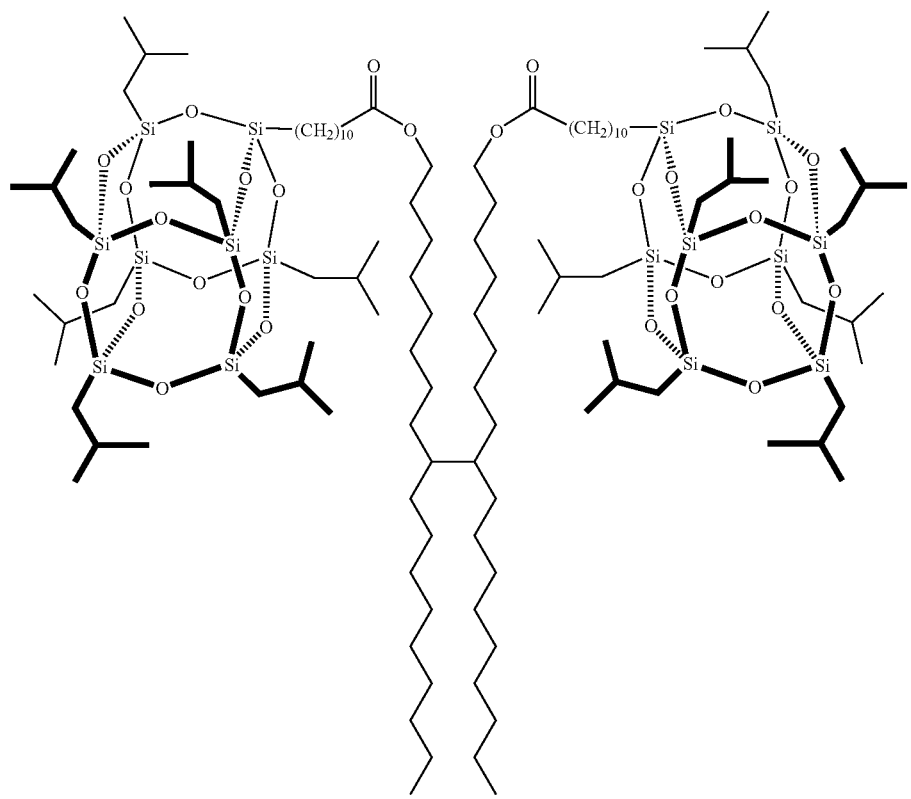
$C_{114}H_{238}O_{28}Si_{16}$
MW = 2506.46

Example 3

Preparation of Wax-Functionalized POSS Nanoparticles

A mixture of [Ethyl Undecanoate]-Isobutyl-POSS (from Hybrid Plastics, 4.0 mmol, 4.12 grams), 1,12-dodecanediol (2.0 mmol, 0.40 grams), and para-toluenesulfonic acid as catalyst (0.10 mmol, 0.02 grams) in 30 mL of toluene was heated to reflux for about 8 hours. The mixture was then cooled to room temperature, diluted with 30 mL ethyl acetate and washed with deionized water to remove acid catalyst, then with brine solution. The ethyl acetate extract was dried over anhydrous magnesium sulfate, filtered and concentrated to afford a transparent solid in quantitative yield. $^1$H-NMR spectroscopy confirmed formation of the product. The reaction scheme is shown below.

Example 4

Preparation of Wax-Functionalized POSS Nanoparticles

A mixture of [1,2-Propane Diol]-Isobutyl-POSS (from Hybrid Plastics; 1.9 grams, 2.0 mmol), stearic acid (4.5 mmol, 1.28 grams), and para-toluenesulfonic acid as catalyst (0.20 mmol, 0.04 grams) in 50 mL of toluene is heated to reflux for about 5 hours. The mixture is cooled, extracted into 100 mL ethyl acetate and washed with deionized water, then with dilute sodium bicarbonate solution (10% NaHCO$_3$), and lastly with brine solution. The ethyl acetate extract is removed and dried over anhydrous magnesium sulfate, filtered and concentrated to provide a wax-like semi-solid in quantitative yield. The reaction scheme is shown below.

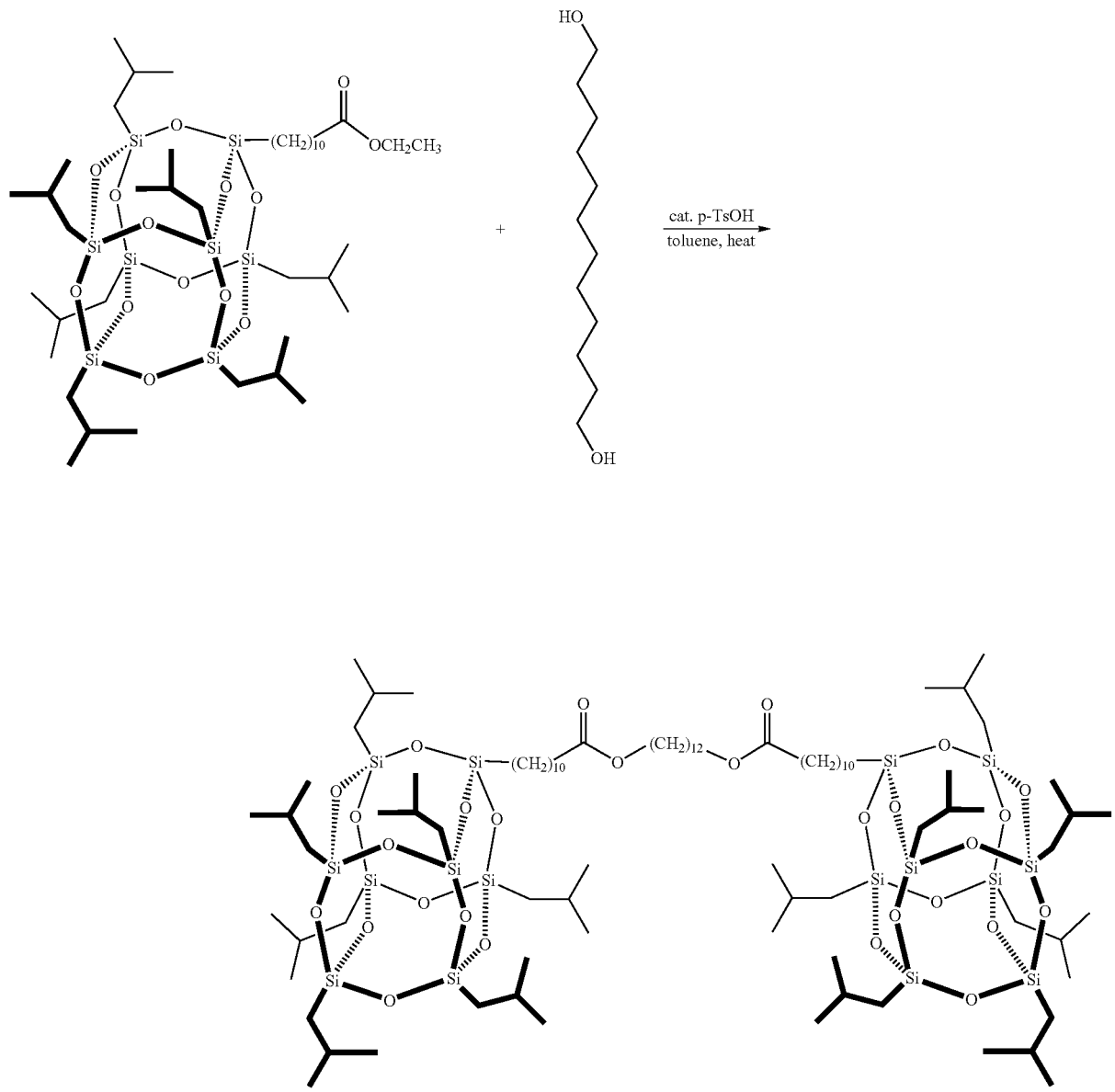

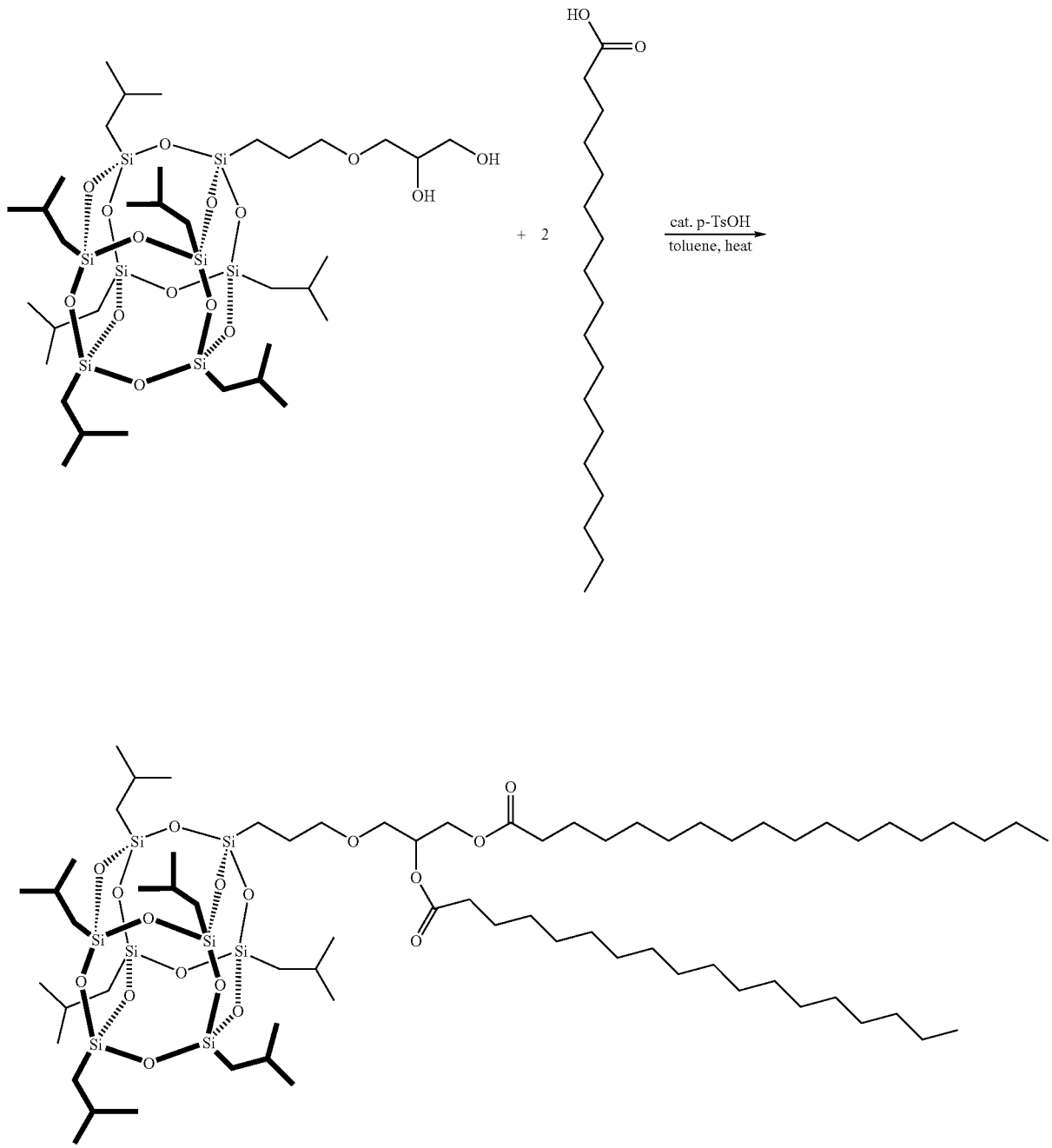

Example 5

Preparation of Wax-Functionalized POSS Nanoparticles

A solution containing [3-Aminopropyl]-Isobutyl-POSS (from Hybrid Plastics; 2.0 mmol, 1.75 grams) dissolved into 30 mL anhydrous toluene is stirred under inert atmosphere. A second solution containing stearyl isocyanate (2.1 mmol, 0.62 grams) dissolved in 15 ml of anhydrous toluene is slowly dripped into the POSS solution at room temperature, after which the resulting mixture is stirred at room temperature for an additional 2 hours. Solvents from the crude reaction mixture is removed by distillation in vacuo, producing a wax-like semi-solid in quantitative yield. The reaction scheme is shown below.

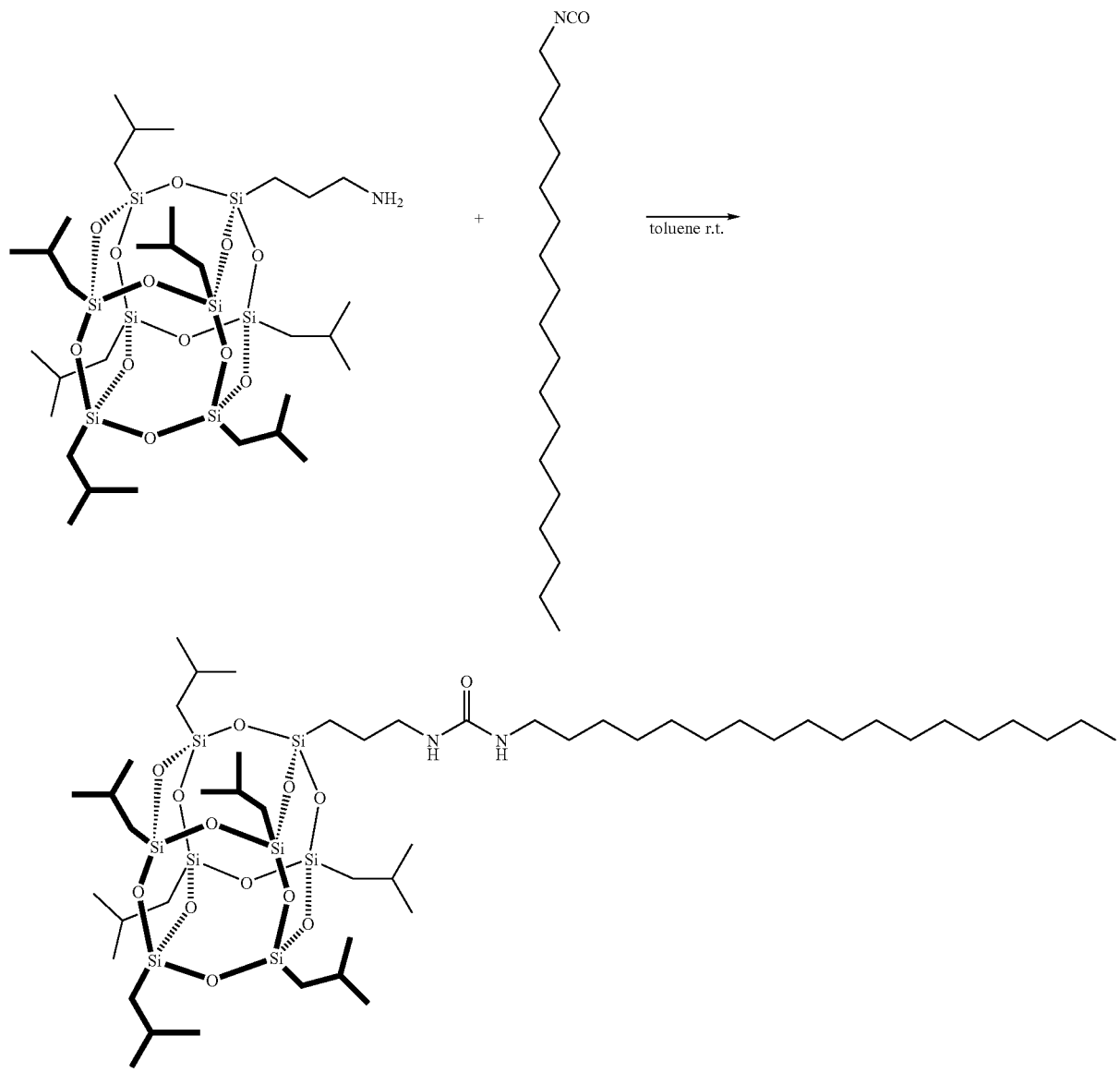

Example 5

Phase-Change Ink Compositions Containing Wax-Modified POSS Nanoparticles

Several phase-change/solid ink compositions are disclosed which comprise wax-modified POSS nanoparticles at a loading in the range of 2-wt % to about 20-wt %. Three examples are provided of low-energy/low-melting solid ink vehicles only, i.e. without colorant and other ink components—in one example containing about 2-wt % of Octaisodecyl POSS nanoparticles, in another example containing about 5 wt % of Octaisodecyl POSS nanoparticles, and in yet another example containing about 10 wt % of wax-modified nanoparticles from example 1. Two examples of cyan colored solid inks are described, in one example containing about 10-wt % of POSS particles from Example 1, in another example containing about 5-wt % of POSS particles from Example 1 and one example of a yellow colored solid ink is described containing i about 10 wt % of Octaisobutyl POSS.

Ink Vehicle Example 1: A phase change solid ink vehicle containing 2-wt % of Octaisobutyl POSS particles was prepared by adding 4.66 grams (46.57 wt %) of polyethylene wax (PE 500, available from Baker Petrolite, Tulsa, Okla., a polyethylene wax with an average chain length of 36 hydrocarbons) and 5.14 grams (51.43 wt %) of UNILIN® 425 with an average chain length of 30 hydrocarbons (available from Baker Petrolite, Tulsa, Okla.), in a beaker. The materials were melted together at a temperature of about 110° C. in a heated reaction block and stirred for 0.5 hrs at 500 rpm. To this mixture was then added 0.2 gram (2 wt %) of Octaisobutyl-POSS (available from Aldrich Fine Chemicals) and the temperature was increased to 120° C. The mixture was stirred for an additional 1 hr and then cooled to room temperature.

Ink Vehicle Example 2: A phase change solid ink vehicle containing 5-wt % Octaisobutyl-POSS was prepared as in Ink Vehicle Example 1 except that the temperature was raised to 140° C. after addition of POSS. The vehicle thus prepared exhibited a viscosity of 8.3 centipoise as measured by an RFS3 Rheometrics parallel-plate viscometer at 110° C.

Ink Vehicle Example 3: A phase change solid ink vehicle containing 10-wt % wax-modified POSS from Example 1 is prepared as described for Ink Vehicle Example 2.

TABLE 1

Phase change solid ink vehicles with wax-modified POSS particles

| | Comparative Ink Vehicle Wt (%) | Ink vehicle 1 Wt (%) | Ink vehicle 2 Wt (%) | Ink Vehicle 3 wt (%) |
|---|---|---|---|---|
| Polwax 500 | 47.52 | 46.57 | 45.14 | 42.76 |
| Unilin 425 | 52.48 | 51.43 | 49.86 | 47.24 |
| Octaisobutyl-POSS | 0.00 | 2.00 | 5.00 | 0 |
| Wax Modified POSS from Example 1 | 0 | 0 | 0 | 10.00 |
| Total | 100.00 | 100.00 | 100.00 | 100.00 |
| Viscosity at 100° C. | 7.15 cps | — | 8.30 cps | — |

Addition of the POSS particles in the ink vehicles did not result in a large increase in viscosity (only 1.15 cps increase after adding 5 wt % of POSS particles). This is a good indication that the ink can tolerate a higher loading of POSS nanoparticles in order to improve ink robustness.

Ink Example 1: A cyan ink composition is prepared as follows: (1) adding in a beaker while mixing in the temperature range of 40 to 70 degrees C. the following components (a) to (e): (a) 55.38 grams of UNILIN® 425 (a linear primary long chain alcohol, obtained from Baker Petrolite, Tulsa, Okla., with an average chain length of 30 hydrocarbons), (b) 7.09 grams of a glycerol ester of hydrogenated rosin acid (KE-100, obtained from Arakawa Chemical Industries, Ltd, Osaka, Japan), (c) 5.08 gram of an alkylbenzyl phthalate of the formula

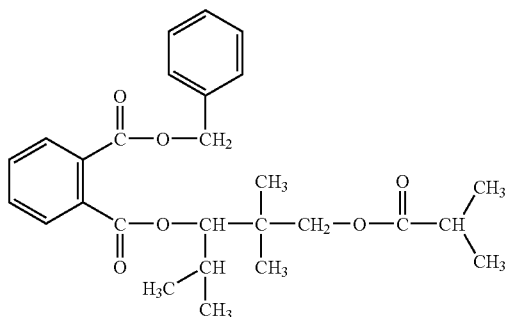

(SANTICIZER® 278, obtained from Ferro Corporation, Bridgeport, N.J.), (d) 0.17 gram of NAUGUARD® 445 antioxidant (obtained from Uniroyal Chemical Co., Middlebury, Conn.), and (e) 2.18 grams of a triamide resin described in U.S. Pat. No. 6,860,930, the disclosure of which is totally included here by reference; to 16.25 g of a dispersion of the wax-modified POSS particles from Example 2 (40% dispersion in toluene, (2) stirring the dispersion obtained in (1) for an additional 2 hours; (3) increasing the temperature to about 100 degrees C., the toluene solvent being slowly evaporated until a viscous solution is obtained; (4) the temperature of the viscous solution is further increased to about 135 degrees C. to facilitate the dissolution/melting of the ink components; (5) the temperature is maintained at 135 degrees C. until a clear and homogeneous solution is obtained and all the toluene is removed from the ink; (6) 50.13 grams of polyethylene wax (PE 500, obtained from Baker Petrolite, Tulsa, Okla.) was slowly added to the hot dispersion, and the dispersion stirred for an additional 2 hours at about 500 rpm; (7) 3.47 grams of the cyan colorant disclosed in Example VIII of U.S. Pat. No. 6,472,523, the disclosure of which is totally incorporated herein by reference, is added, the ink is stirred for about 2 additional hours at 135 degrees C. and then cooled to room temperature.

Ink Example 2: A cyan phase change solid ink is prepared as described in Ink Example 1 except that 10 wt % of the wax-modified POSS from Example 1 is used. Relative amounts of the ingredients in this ink expressed in wt %, are indicated in Table 2 below.

Ink Example 3: A yellow phase change solid ink is prepared as described in Ink Example 1 except that 10 wt % of the Octaisobutyl POSS is used and a yellow colorant described in U.S. Pat. No. 6,713,614. Relative amounts of the ingredients in this ink expressed in wt %, are indicated in Table 2 below.

TABLE 2

Phase change solid inks with wax-modified POSS particles

| | Ink Example 1 Wt (%) | Ink Example 2 Wt (%) | Ink Example 3 Wt (%) |
|---|---|---|---|
| Polwax 500 | 38.56 | 36.53 | 36.53 |
| Unilin 425 | 42.60 | 40.36 | 40.36 |
| Wax Modified POSS from Example 2 | 5.00 | 0.00 | 0.00 |
| Wax Modified POSS from Example 1 | 0.00 | 10.00 | 0.00 |
| Octaisobutyl POSS | 0.00 | 0.00 | 10.00 |
| KE-100 | 5.45 | 5.16 | 5.16 |
| Tri-Amide Resin | 1.68 | 1.59 | 1.59 |
| Santicizer 278 | 3.91 | 3.71 | 3.71 |
| Nauguard 445 | 0.13 | 0.12 | 0.12 |
| Cyan Dye | 2.67 | 2.53 | 0.00 |
| Yellow Dye | 0.00 | 0.00 | 2.53 |
| Total | 100.00 | 100.00 | 100.00 |

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A hydrophobically- or hydrophilically-functionalized polyhedral oligomeric silsesquioxane, having the following formula:

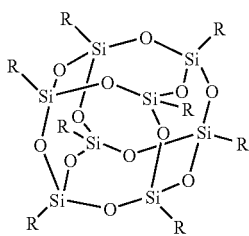

wherein each R, which may be the same or different, independently represents a linear, branched or cyclic organic group selected from the group consisting of hydrophobic alkyl groups, hydrophobic aryl groups, hydrophobic arylalkyl groups, hydrophobic cycloaliphatic groups, and hydrophilic organic moieties, provided that at least one of the R groups is a wax-like aliphatic group which comprises: about 10 to about 100 carbon atoms, and from 1 to about 10 reactive functional groups.

2. The hydrophobically-functionalized polyhedral oligomeric silsesquioxane of claim 1, wherein each R group that is not a wax-like aliphatic group independently represents a substituted or unsubstituted aliphatic or aromatic hydrocarbon group having from 1 to about 50 carbon atoms, wherein the hydrocarbon group can be cyclic, branched or linear chained, are saturated or unsaturated, and unsubstituted or substituted with one or more groups selected from the group consisting of halogen, methyl, ethyl, isobutyl, isooctyl, cyclopentyl, cyclohexyl, vinyl, styryl, trimethylsiloxyl, trichlorosilylethyl, trichlorosilylpropyl, dichiorosilylethyl, chlorosilylethyl, phenyl, chlorobenzyl, cyanoethyl, cyanopropyl, norbornenyl, fluoro, silanol, dimethylsilane, alkoxy, (meth)acrylate, silane, aniline, amine, phenol, and alcohol.

3. The hydrophobically-functionalized polyhedral oligomeric silsesquioxane of claim 1, wherein the wax-like aliphatic group is selected from the group consisting of saturated linear aliphatic hydrocarbons; unsaturated linear hydrocarbons; short saturated aliphatic group, either linear, branched or containing cyclic groups; and mixtures thereof.

4. The hydrophobically-functionalized polyhedral oligomeric silsesquioxane of claim 1, wherein the wax-like aliphatic group is selected from the group consisting of poly (alkylene) wax like polyethylene, polypropylene, polybutadiene, polyisoprene, hexadecyl, octadecyl, eicosanyl, docosanyl, tetracosanyl, hexacosanyl, octacosanyl, triacontanyl, hexatriacontanyl, C-36 dimer diol, C-36 dimer diacid, and mixtures thereof.

5. The hydrophobically-functionalized polyhedral oligomeric silsesquioxane of claim 1, wherein a ratio of POSS moieties to wax-like aliphatic groups is from about 1:1 to about 1:4.

6. The hydrophilically-functionalized polyhedral oligomeric silsesquioxane of claim 1, wherein at least one of the R groups is a hydrophilic group.

7. A nanostructure comprising a plurality of functionalized polyhedral oligomeric silsesquioxane particles or claim 1, arranged into a substantially lamellar structure.

8. The hydrophobically-functionalized polyhedral oligomeric silsesquioxane of claim 1, wherein the wax-like aliphatic group comprises about 12 to about 50 carbon atoms.

9. The hydrophobically-functionalized polyhedral oligomeric silsesquioxane of claim 1, wherein the wax-like aliphatic group comprises about 16 to about 40 carbon atoms.

10. The hydrophobically-functionalized polyhedral oligomeric silsesquioxane of claim 2, wherein the wax-like aliphatic group is more hydrophobic that the polyhedral oligomeric silsesquioxane.

11. The hydrophobically-functionalized polyhedral oligomeric silsesquioxane of claim 2, wherein only one of the R groups is a wax-like aliphatic group.

12. The hydrophobically-functionalized polyhedral oligomeric silsesquioxane of claim 2, wherein at least two of the R groups are independently a wax-like aliphatic group.

13. The hydrophilically-functionalized polyhedral oligomeric silsesquioxane of claim 6, wherein the hydrophilic group is selected from the group consisting of acid polar groups, basic polar groups, and neutral polar groups.

14. The hydrophilically-functionalized polyhedral oligomeric silsesquioxane of claim 6, wherein the hydrophilic group is selected from the group consisting of carboxylic acid and derivative groups, sulfonic acid and derivative groups, phosphoric acid and derivative groups, formyl groups, amino groups, amide groups, ester groups, hydroxyl groups, alkoxyl groups, halo groups, nitrile groups, and cyano groups.

15. The nanostructure of claim 7, wherein the hydrophobically-functionalized polyhedral oligomeric silsesquioxane particles are self-arranged into the substantially lamellar structure.

16. The nanostructure of claim 7, wherein the substantially lamellar structure comprises a plurality of lamellar sheets, with a distance between adjacent sheets being about 1 to about 100 nm.

17. An ink composition comprising:
a carrier,
a colorant, and
a hydrophobically- or hydrophilically-functionalized polyhedral oligomeric silsesquioxane as a reinforcing agent,
wherein the hydrophobically- or hydrophilically-functionalized polyhedral oligomeric silsesquioxane has the following formula:

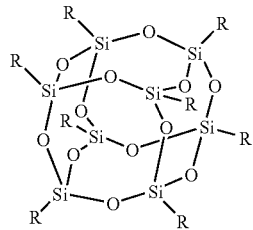

wherein each R, which may be the same or different, independently represents a linear, branched or cyclic organic group selected from the group consisting of hydrophobic alkyl groups, hydrophobic aryl groups, hydrophobic arylalkyl groups, hydrophobic cycloaliphatic groups, and hydrophilic organic moieties,
provided that at least one of the R groups is a wax-like aliphatic group which comprises: about 10 to 100 carbon atoms, and from 1 to about 10 reactive functional groups,
wherein the carrier is present in an amount of about 50 to about 99.9 weight %, said colorant is present in an amount of about 0.1 to about 50 weight % by weight of the ink, and said reinforcing agent is present in an amount of from about 1 to about 50 weight % by weight of the ink, and
the ink composition is selected from the group consisting of solid ink compositions, phase change ink compositions, curable ink compositions, and aqueous ink compositions.

18. The ink composition of claim 17, wherein the carrier comprises one or more organic compounds that are solid at room temperature but becomes liquid at a printer operating temperature for ejecting the ink composition onto a print surface.

19. The ink composition of claim 17, wherein the carrier is selected from the group consisting of amides, isocyanate-derived resins and waxes, paraffins, microcrystalline waxes, polyethylene waxes, ester waxes, amide waxes, fatty acids, fatty alcohols, fatty amides and other waxy materials, sulfonamide materials, resinous materials made from different natural sources, and synthetic resins, oligomers, polymers and copolymers, and mixtures thereof.

20. The ink composition of claim 17, further comprising at least one additive selected from the group consisting of surfactants, light stabilizers, UV absorbers, optical brighteners, thixotropic agents, dewetting agents, slip agents, foaming agents, antifoaming agents, flow agents, oils, plasticizers, binders, electrical conductive agents, fungicides, bactericides, organic and inorganic filler particles, leveling agents, opacifiers, antistatic agents, dispersants, and mixtures thereof.

21. The ink composition of claim 17, wherein the wax-like aliphatic group comprises about 12 to about 50 carbon atoms.

22. The ink composition of claim 17, wherein the wax-like aliphatic group comprises about 16 to about 40 carbon atoms.

23. A method of making a hydrophobically- or hydrophilically-functionalized polyhedral oligomeric silsesquioxane, comprising reacting a polyhedral oligomeric silsesquioxane raw compound that contains at least one chemical functional group that can be readily transformed into one or more waxy aliphatic chains, with a suitable reagent to provide a wax-like aliphatic group at the reaction site,
wherein the hydrophobically- or hydrophilically-functionalized polyhedral oligomeric silsesquioxane has the following formula:

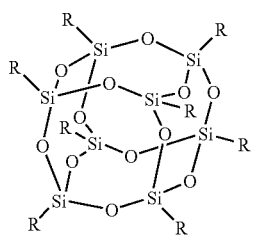

wherein each R, which may be the same or different, independently represents a linear, branched or cyclic organic group selected from the group consisting of hydrophobic alkyl groups, hydrophobic aryl groups, hydrophobic arylalkyl groups, hydrophobic cycloaliphatic groups, and hydrophilic organic moieties,
provided that at least one of the R groups is a wax-like aliphatic group
which comprises: about 10 to about 100 carbon atoms, and from 1 to about 10 reactive functional groups.

24. The method of claim 23, wherein the at least one chemical functional group on the polyhedral oligomeric silsesquioxanes compound raw material is selected from the group consisting of a carboxylic acid derivative which includes carboxylic acid, ester, acid anhydride, isocyanate, phthalimide or amide, an alcohol, an amine, and a halogen and the reagent is selected from the group consisting of unsaturated hydrocarbon monocarboxylic acids, unsaturated monocarboxylic acid waxes, branched saturated or unsaturated monocarboxylic acid waxes, saturated hydrocarbon alcohols, linear unsaturated primary alcohols, branched saturated primary alcohols, saturated hydrocarbon amines, branched saturated primary amines, other monofunctional hydrocarbon waxes with the same hydrocarbon structure above and wherein the functional group is a carboxylic acid derivative, difunctional hydrocarbon waxes, and mixtures thereof.

25. The method of claim 23, wherein the reagent is selected from the group consisting of hexadecanoic acid, palmitic acid, heptadecanoic acid, octadecanoic acid, stearic acid, eicosanoic acid, arachidic acid, docosanoic acid, or behenic acid, tetracosanoic acid, lignoceric acid, hexacosanoic acid, cerotic acid, heptacosanoic acid, octacosanoic acid, montanic acid, triacontanoic acid, dotriacontanoic acid, tritriacontanoic acid, tetratriacontanoic acid, pentatriacontanoic acid, mixtures of long chain saturated carboxylic acids that have greater than 30 carbon atoms, oleic acid, linoleic acid, erucic acid, 2-decyltetradecanoic acid, isostearic acid, dodecanol, tetradecanol, hexadecanol, octadecanol, isostearyl alcohol, eicosanol, docosanol, tetracosanol, mixtures of linear primary alcohols 24 to 50 carbon atoms, blends of saturated primary alcohols with more than 20 carbon atoms, hexadecenyl alcohol, octadecenyl alcohol, linoleyl alcohol, isostearyl alcohol, 2-hexyldecanol, iso-arachidyl alchol, 2-tetradecyloctadecanol, branched primary alcohols with 18 carbon atoms, $C_{36}$-dimer diol mixtures with 36 carbon atoms dodecylamine, octadecylamine, tetradecyl-dodecyloxypropylamine, iso-stearylamine, 3-aminopropylether-functionalized branched alcohols, stearyl isocyanate, $C_{36}$-dimer diisocyanate, methyl oleate, methyl stearate, methyl octacosanoate, lauryl palmitoleate, 1,12-dodecanedioic acid, 1,15-pentadecanedioic acid, 1,18-octadecanedioic acid, 8-oxo-pentadecanedioic acid, 1,18-octadecanedioic acid, docosanedioic acid, $C_{36}$-dimer diacid mixtures with 36 carbon atoms, 1,18-octadecanediol, 1,18 Octadec-9-en-diol, $C_{36}$-dimer diol mixtures with 36 carbon atoms, $C_{36}$-dimer diamines, polyether diamines, and mixtures thereof.

26. The method of claim 23, wherein the reaction is conducted in the presence of a catalyst.

27. The method of claim 23, wherein an equivalents ratio of polyhedral oligomeric silsesquioxane raw compound to reagent is from about 1:1 to about 1:3.

* * * * *